(12) United States Patent
Olovsson

(10) Patent No.: US 10,201,767 B2
(45) Date of Patent: Feb. 12, 2019

(54) CHROMATOGRAPHY SYSTEM AND METHOD

(71) Applicant: GE Healthcare Bio-Sciences AB, Uppsala (SE)

(72) Inventor: Bjorn Olovsson, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 253 days.

(21) Appl. No.: 15/104,187

(22) PCT Filed: Dec. 15, 2014

(86) PCT No.: PCT/SE2014/051498
§ 371 (c)(1),
(2) Date: Jun. 13, 2016

(87) PCT Pub. No.: WO2015/094094
PCT Pub. Date: Jun. 25, 2015

(65) Prior Publication Data
US 2016/0310870 A1    Oct. 27, 2016

(30) Foreign Application Priority Data

Feb. 19, 2013    (SE) ..................................... 1351524

(51) Int. Cl.
| | | |
|---|---|---|
| *B01D 15/18* | (2006.01) | |
| *F16K 11/074* | (2006.01) | |
| *G01N 30/20* | (2006.01) | |
| *G01N 30/46* | (2006.01) | |

(Continued)

(52) U.S. Cl.
CPC ..... *B01D 15/1842* (2013.01); *B01D 15/1814* (2013.01); *B01D 15/1821* (2013.01); *F16K 11/074* (2013.01); *F16K 11/076* (2013.01); *G01N 30/20* (2013.01); *G01N 30/468* (2013.01); *G01N 30/6034* (2013.01);
(Continued)

(58) Field of Classification Search
CPC ...................... B01D 15/1842; B01D 15/1814
USPC .............................................. 73/61.56, 23.41
See application file for complete search history.

(56) References Cited

U.S. PATENT DOCUMENTS

| | | |
|---|---|---|
| 4,632,149 A | 12/1986 | Oroskar et al. |
| 5,630,943 A | 5/1997 | Grill |
| 5,770,088 A | 6/1998 | Ikeda et al. |

(Continued)

FOREIGN PATENT DOCUMENTS

| | | |
|---|---|---|
| EP | 3082991 A1 | 10/2016 |
| WO | 2010151214 A1 | 12/2010 |

(Continued)

OTHER PUBLICATIONS

International Search Report and Written Opinion regarding International Application No. PCT/SE2014/051498, dated Mar. 18, 2015, 15 pages.

(Continued)

*Primary Examiner* — John Fitzgerald
*Assistant Examiner* — Rodney T Frank
(74) *Attorney, Agent, or Firm* — Wood IP LLC

(57) ABSTRACT

A chromatography system comprising at least two chromatography columns, where a feed recirculation of outflow from a primary load column to the inlet of a secondary load column is combined such that the feed recirculation outflow from all columns that will be used as primary load columns in the system will pass through one and the same feed recirculation flow path.

9 Claims, 18 Drawing Sheets

(51) Int. Cl.
*G01N 30/60* (2006.01)
*F16K 11/076* (2006.01)

(52) U.S. Cl.
CPC .. *B01D 2215/023* (2013.01); *B01D 2215/024* (2013.01); *G01N 2030/202* (2013.01)

(56) References Cited

U.S. PATENT DOCUMENTS

| | | |
|---|---|---|
| 6,325,940 B1 | 12/2001 | Ikeda |
| 2006/0273013 A1 | 12/2006 | Chin et al. |
| 2010/0206812 A1 | 8/2010 | Woods et al. |
| 2011/0067770 A1 | 3/2011 | Pederson et al. |
| 2012/0091063 A1 | 4/2012 | Bangtsson et al. |

FOREIGN PATENT DOCUMENTS

| | | |
|---|---|---|
| WO | 2015/094094 A1 | 6/2015 |
| WO | 2015/094095 A1 | 6/2015 |
| WO | 2015/144481 A1 | 10/2015 |

OTHER PUBLICATIONS

International-Type Search Report regarding SE Application No. SE1351524-2, dated Jul 1, 2014, 5 pages.
International Preliminary Report on Patentability Received for PCT Patent Application No. PCT/SE2014/051498, dated Jun. 21, 2016, 8 Pages.
Office Action Received for Chinese Patent Application No. 201480075888.3, dated Apr. 25, 2017, 14 pages (7 Pages of English Translation + 7 pages Official copy).
Extended European Search Report Received for European Patent Application No. 14870681.5, dated Jul. 4, 2017, 8 pages.

CHROMATOGRAPHY SYSTEM AND METHOD

CROSS-REFERENCE TO RELATED APPLICATIONS

This application is a filing under 35 U.S.C. 371 of international application number PCT/SE2014/051498, filed Dec. 15, 2014, which claims priority to SE application number 1351524-2, filed Dec. 19, 2013, the entire disclosures of each of which are hereby incorporated by reference.

FIELD OF THE INVENTION

The present invention relates to a chromatography system and a method in a chromatography system.

BACKGROUND OF THE INVENTION

In continuous chromatography, several identical columns are connected in an arrangement that allows columns to be operated in series and/or in parallel, depending on the method requirements. Thus, all columns can be run in principle simultaneously, but slightly shifted in method steps. The procedure can be repeated, so that each column is loaded, eluted, and regenerated several times in the process. Compared to 'conventional' chromatography, wherein a single chromatography cycle is based on several consecutive steps, such as loading, wash, elution and regeneration, in continuous chromatography based on multiple identical columns all these steps occur simultaneously but on different columns each. Continuous chromatography operation results in a better utilization of chromatography resin, reduced processing time and reduced buffer requirements, all of which benefits process economy. Continuous chromatography is sometimes denoted simulated moving bed (SMB) chromatography or periodic counter current.

U.S. Pat. No. 6,325,940 (Daicel) relates to a simulated moving bed chromatographic system comprising packed beds filled with separating fillers, by which the separation performance of the packed beds can be evaluated without removing the packed beds from the circular fluid passage. As the packed beds can be evaluated without removal thereof, the system can be examined on whether the deterioration of the system is caused by the columns or not, and, if yes, which column causes the deterioration. The system comprises at least four packed beds connected in series and endlessly to each other and ports for adding and taking out fluid.

When connecting a number of chromatography columns in a simulated moving bed system there is a need for many valves and many tubes connecting the outlet of each column to the inlets of each of the other columns. In FIG. 1 a prior art simulated moving bed system 1 provided by GE Healthcare is shown. Four columns 3a,3b,3c,3d are connected in this simulated moving bed system. The outlets of each of the chromatography columns 3a,b,c,d can be connected to the inlets of each of the other columns in the system. These column connections are given number 5 in FIG. 1 and are provided through inlet and outlet valves which are provided to the inlets and outlets of each column. The Inlet and outlet valves comprise ports and control capabilities such that the correct valve ports are open at the right time, i.e. such that the flow into and out from the columns are directed correctly according to a simulated moving bed process. There is a need for an improved simulated moving bed system with regard to the numerous and complicated valves and tubes provided in the system.

SUMMARY OF THE INVENTION

An object of the invention is to provide an improved chromatography system and method.

This is achieved in a chromatography system comprising at least two chromatography columns, where a feed recirculation of outflow from a primary load column to the inlet of a secondary load column is combined such that the feed recirculation outflow from all columns that will be used as primary load columns in the system will pass through one and the same feed recirculation flow path.

This is also achieved in a method for recirculating outlet flow from a primary load column to the inlet of a secondary load column in a chromatography system comprising at least two chromatography columns, said method comprising combining the feed recirculation for all columns that will be used as primary load columns in the system such that the feed recirculation flow will pass through one and the same feed recirculation flow path.

Hereby the number and total length of tubes in the system can be decreased considerably.

In one embodiment of the invention a feed recirculation detector is provided in the feed recirculation flow path. The method comprises in this embodiment detecting an effluent signal being representative of the composition of the feed recirculation in the feed recirculation flow path.

Hereby the total number of detectors needed in the system can be decreased and the total cost of the system is decreased.

In one embodiment of the invention the system comprises a feed recirculation flow uniter connected to outlet valves provided to outlets from each of the columns that will be used as primary load column, whereby the outlet flow from the columns is controlled such that it is provided to the feed recirculation flow uniter when the column is used as primary load column, said system further comprising a feed recirculation flow splitter connected to the feed recirculation flow uniter through the feed recirculation flow path and further connected to inlet valves provided to inlets to each of the columns that will be used as primary load column, whereby the system is arranged to control the flow from the feed recirculation flow splitter to enter the column that presently serves as secondary load column.

In this embodiment the method further comprises directing outflow from each of the columns when they are serving as primary load column to a feed recirculation flow uniter connected to outlet valves provided to outlets from each of the columns that will be used as primary load column, transferring said outflow from the feed recirculation flow uniter through the feed recirculation flow path to a feed recirculation flow splitter connected to inlet valves provided to inlets to each of the columns that will be used as primary load column, and controlling the flow from the feed recirculation flow splitter to enter the column that presently serves as secondary load column.

In another embodiment of the invention the system comprises a feed recirculation means connected to outlet valves provided to outlets from each of the columns that will be used as primary load column, whereby the outlet flow from the columns is controlled such that it is provided to the feed recirculation means when the column is used as primary load column, said feed recirculation means further being connected to inlet valves provided to inlets to each of the columns that will be used as primary load column, whereby the system is arranged to control the flow from the feed recirculation means to enter the column that presently serves as secondary load column, said feed recirculation means further comprising a feed recirculation flow path through which all feed recirculation flow will pass.

In one embodiment of the invention the system comprises
   a column inlet rotary valve connected to the inlets of all columns that will be used as primary load columns in the system and to at least three inflows,
   a column outlet rotary valve connected to the outlets of all columns that will be used as primary load columns in the system and to at least three outflows,
wherein the feed recirculation flow path connects the inlet rotary valve with the outlet rotary valve. Hereby the number of valves in the system is considerably decreased.

In another embodiment of the invention the system comprises
   a column connection rotary valve connected to the inlets of all columns that will be used as primary load columns in the system and to at least three inflows and connected to the outlets of all columns that will be used as primary load columns in the system and to at least three outflows,
wherein said feed recirculation flow path connects each column outlet to each column inlet through the column connection rotary valve.

BRIEF DESCRIPTION OF THE DRAWINGS

These and other advantages of the present invention will become more apparent as the following description is read in conjunction with the accompanying drawings, wherein:

FIG. 5a shows the design of a rotary valve that can be used in the embodiment of the invention shown in FIG. 4a.

FIGS. 6a-6d shows in more detail the different positions of the rotary valve shown in FIG. 5a.

FIG. 7 shows the design of another embodiment of a rotary valve that can be used in the embodiment shown in FIG. 4a.

FIG. 8 shows the design of another embodiment of a rotary valve that can be used in the embodiment shown in FIG. 4a.

FIG. 9 shows the design of another embodiment of a rotary valve that can be used in the embodiment shown in FIG. 4a.

DETAILED DESCRIPTION OF THE INVENTION

The embodiments of the invention are described with reference to the drawings. The descriptions of the embodiments are exemplary and are not intended to limit the scope of the invention.

Figure 1:
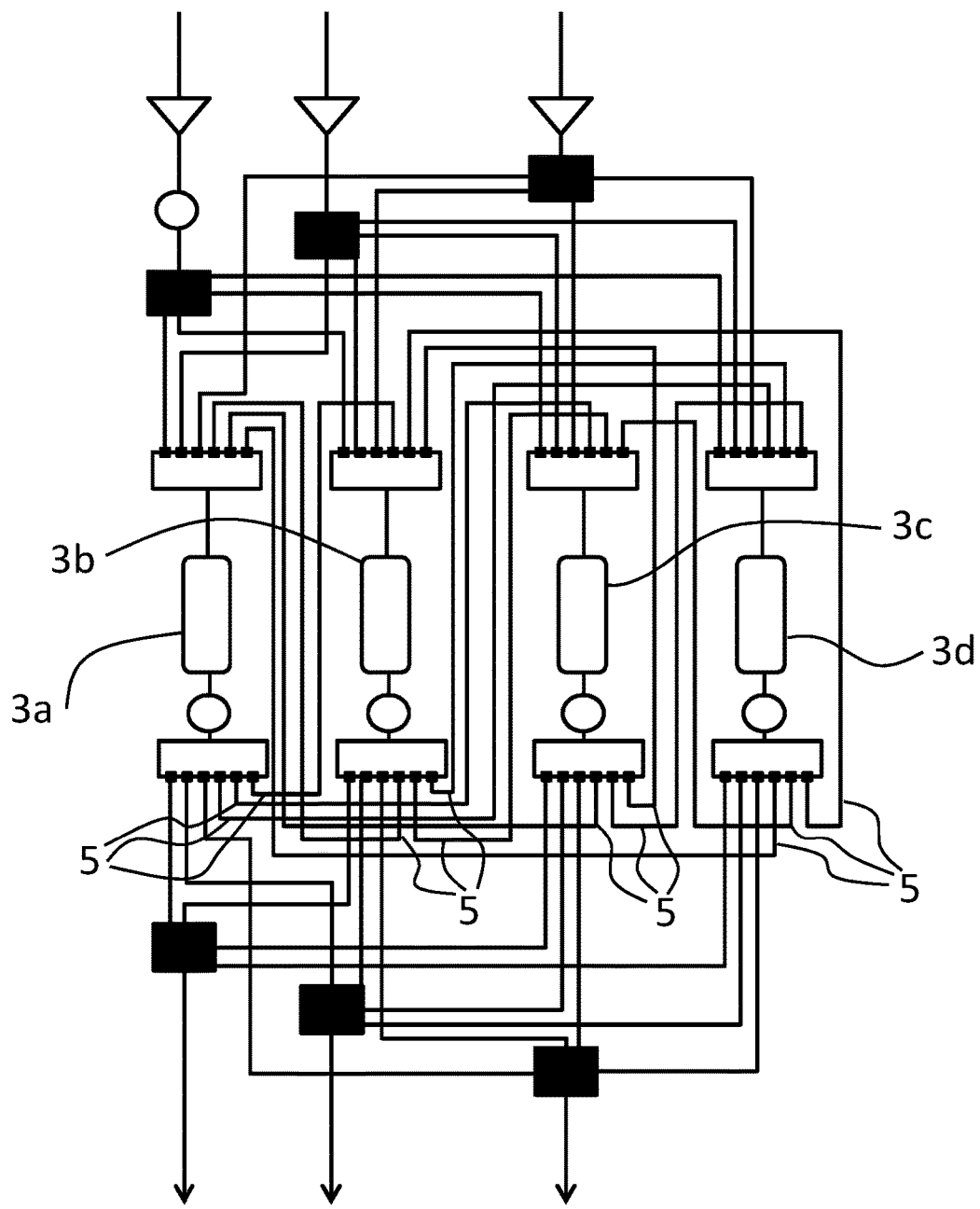
FIG. 1 shows schematically a prior art chromatography system.

FIG. 1 shows schematically a prior art simulated moving bed chromatography system 1 as described above.

Figure 2A:
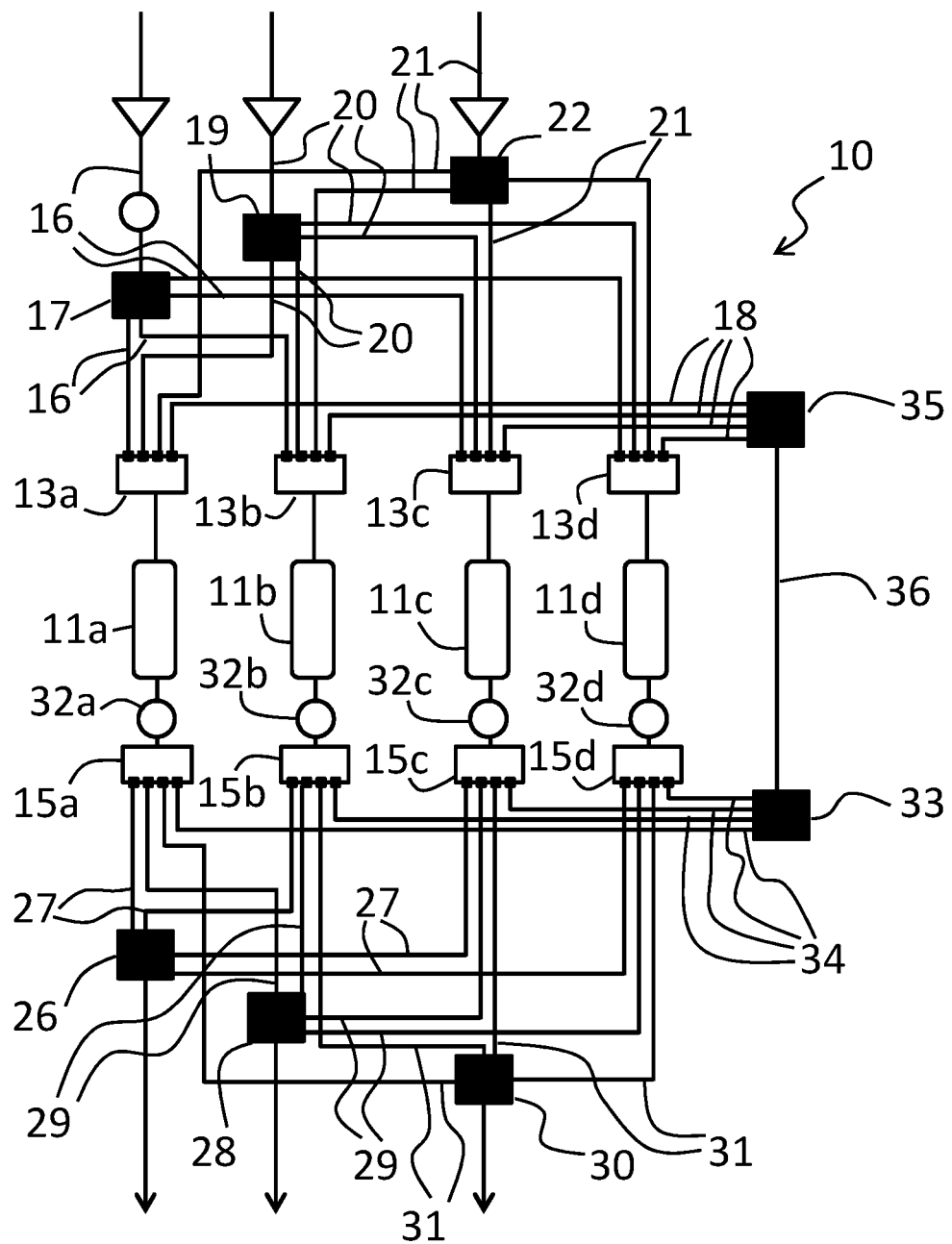
FIG. 2a shows schematically a chromatography system according to one embodiment of the invention.

FIG. 2a shows schematically a simulated moving bed chromatography system 10 according to one embodiment of the invention. Here four chromatography columns are connected in the simulated moving bed chromatography system 10. The number of columns could be varied. Systems with three and two columns will be further described below in relation to FIGS. 3c and 3d. The columns are here called a first chromatography column 11a, a second chromatography column 11b, a third chromatography column 11c and a fourth chromatography column 11d. One inlet valve is provided for each of the columns, a first inlet valve 13a connected to the inlet of the first chromatography column 11a, a second inlet valve 13b connected to the inlet of the second chromatography column 11b, a third inlet valve 13c connected to the inlet of the third chromatography column 11c and a fourth inlet valve 13d connected to the inlet of the fourth chromatography column 11d. Furthermore, one outlet valve is provided for each of the columns, a first outlet valve 15a connected to the outlet of the first chromatography column 11a, a second outlet valve 15b connected to the outlet of the second chromatography column 11b, a third outlet valve 15c connected to the outlet of the third chromatography column 11c and a fourth outlet valve 15d connected to the outlet of the fourth chromatography column 11d.

This is a simulated moving bed system with feed recirculation and therefore the outlets of each of the chromatography columns 11a,b,c,d are connected to the inlets of each of the other columns in the system. This could also be referred to as periodic counter current. The benefit with a feed recirculation is that the risk of losing any possible unbound feed is decreased and therefore the amount of sample provided to the column in the feed can be much higher than in normal chromatography. If there is any unbound sample left after having passed the primary load column it will have another chance to bind in the secondary load column. According to the invention a feed recirculation of outflow from a primary load column to the inlet of a secondary load column is combined for all columns in the system such that at least one part of the feed recirculation from all columns will pass through one and the same feed recirculation flow path 36.

According to this embodiment of the invention the feed recirculation is provided by a feed recirculation flow uniter 33 and a feed recirculation flow splitter 35. A flow splitter and a flow uniter can be for example a manifold or a valve. Each of the outlet valves 15a,b,c,d are connected to the feed recirculation flow uniter 33 through first outflows 34. The feed recirculation flow uniter 33 is in turn connected to the feed recirculation flow splitter 35 by the feed recirculation flow path 36. The feed recirculation flow splitter 35 in turn is connected to each of the inlet valves 13a,b,c,d. According to this embodiment of the invention outlet flows from each of the columns are combined in the first feed recirculation flow splitter 33 and then separated again in the second feed recirculation flow splitter 35 to each of the column inlets. Hereby the number of tubes is decreased compared to a prior art system as for example discussed in relation to FIG. 1 where each column outlet is connected to each one of the other column inlets in the system by separate tubes. The inlet and outlet valves comprise ports and control capabilities such that the correct valve ports are open at the right time, i.e. such that the flow into and out from the columns are directed correctly according to a simulated moving bed method schedule. The outlet flow from the column presently serving as primary load column should be directed through the feed recirculation flow uniter 33 and the feed recirculation flow splitter 35 to the inlet of the column presently serving as secondary load column.

In this embodiment a first inflow 16 is provided to each of the inlet valves through a first flow splitter 17. A second inflow 18 is provided to each of the inlet valves through the feed recirculation flow splitter 35, a third inflow 20 is provided to each of the inlet valves through a second flow splitter 19 and a fourth inflow 21 is provided to each of the inlet valves through a third flow splitter 22. The first inflow is for example in a simulated moving bed system a feed inflow comprising the target sample, the second inflow is for example the feed recirculation flow, the third inflow could be a regeneration buffer used for regenerating the column and the fourth inflow is for example an elution buffer used for the elution chromatography step.

Furthermore, in this embodiment the outlet valves 15a,b,c,d are each connected to the feed recirculation flow uniter 33 through first outflows 34, to a feed outlet flow uniter 26 by second outflows 27, to a regeneration outlet flow uniter 28 by third outflows 29, and to an elution outlet flow uniter 30 by fourth outflows 31.

A schedule for the simulated moving bed method could in one embodiment of the invention be that if the feed is directed to the first column 11a then the outflow from the first column 11a should be directed to the inlet of the second column 11b. The second column 11b hereby serves as a secondary load column. When the first column is fully loaded, which could be measured by for example UV or time, the feed is instead directed directly to the second column 11b and the outflow from the second column 11b is directed to the inlet of the third column 11c, which then serves as the secondary load column. At the same time the first column 11a is eluted by directing the elution buffer (fourth inflow 21) to the inlet of the first column 11a and let the outflow from the first column 11a be directed to the elution outlet flow uniter 30 through the fourth outflow 31. When the feed is directed directly to the third column 11c the second column is eluted and the first column is at the same time regenerated, whereby regeneration buffer is provided by the third inflow 20 to the inlet of the first column 11a and the outflow is directed to regeneration outlet flow uniter 28 by the third outflows 29. The last step in the continuous process is that the first column 11a serves as secondary load column when the feed is directed directly to the fourth column 11d. Then the outflow from the first column 11a is directed to the feed outlet flow uniter 26 through the second outflow 27. This is a known process for simulated moving bed techniques. This process is recycled. The inlet and outlet valves are controlled from a control system such that these above described flows are provided.

Furthermore, a first detector 32a is provided at the outlet form the first column 11a, a second detector 32b is provided at the outlet from the second column 11b, a third detector 32c is provided at the outlet from the third column 11c and a fourth detector 32d is provided at the outlet from the fourth column 11d. Said first, second, third and fourth detectors are adapted to detect an effluent signal being representative of the composition of the outflow from the columns. In one embodiment the detectors are UV detectors, i.e. measuring the UV absorbance of the sample. Other possible types of detectors are measuring pH, conductivity, light scattering, fluorescence, IR or visible light. Measurements of for example the UV absorbance of the outlet flow from the columns are used by the control system to control the valves. The UV absorbance can be monitored and used as an indicator for when a column is fully loaded. This is well known in the art and will not be described further here. This is for example described in US 20120091063-A1.

Figure 2B:
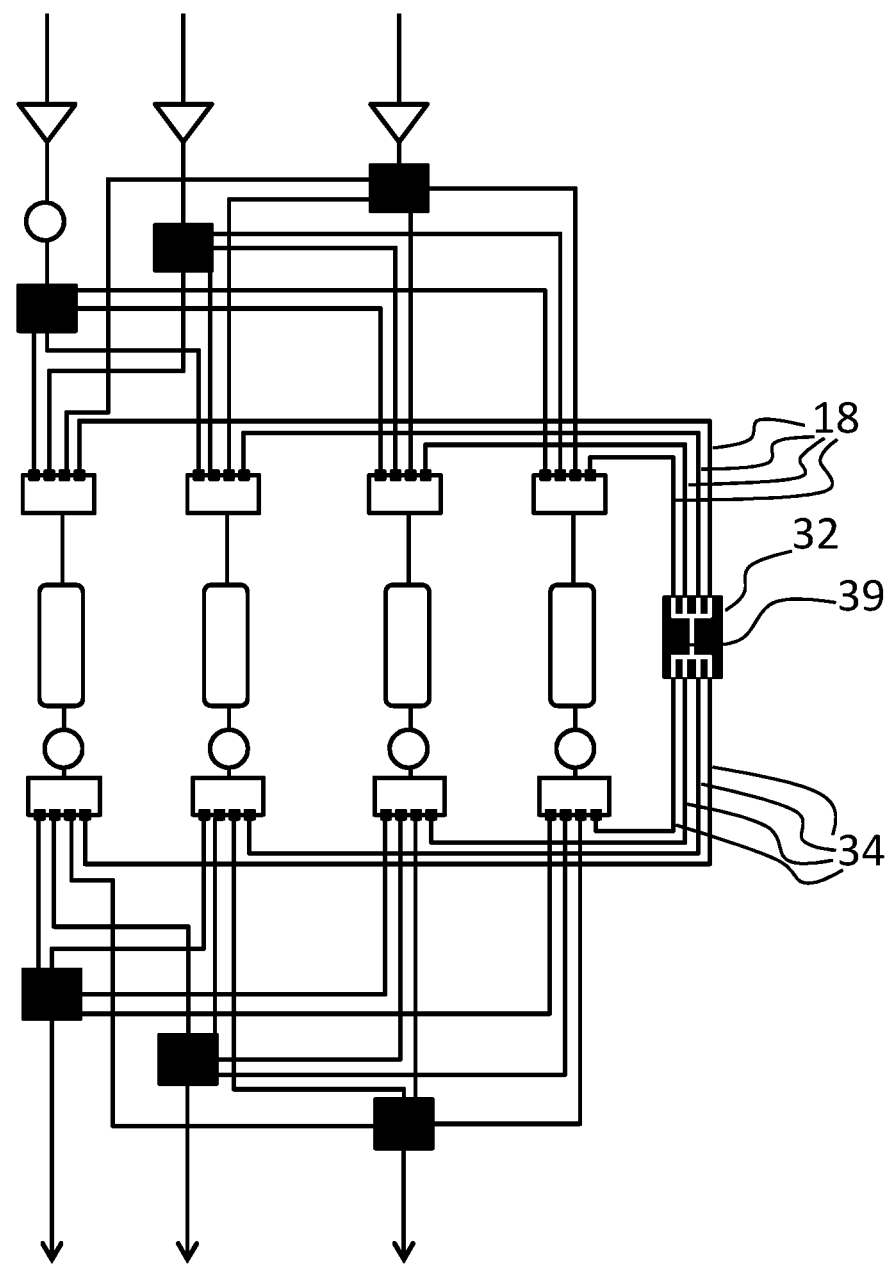
FIG. 2b shows schematically a chromatography system according to one embodiment of the invention.

FIG. 2b shows another embodiment of the invention. This embodiment is similar to the embodiment shown in FIG. 2a and the details will not be described here. However, the feed recirculation flow uniter 33 and feed recirculation flow splitter 35 are in this embodiment replaced by one device, a feed recirculation means 32 incorporating both the functions of the feed recirculation flow uniter 33 and the feed recirculation flow splitter 35 of FIG. 2a. This feed recirculation means 32 is connected to all the column outlets and inlets and it has the function of both combining all the first outflows 34 into one flow inside the feed recirculation means 32 and to divide this flow into all the separate column inlets as second inflows 18. Inside the feed recirculation means 32 there is a common feed recirculation flow path 39 through which all feed recirculation flow will pass.

Figure 3A:
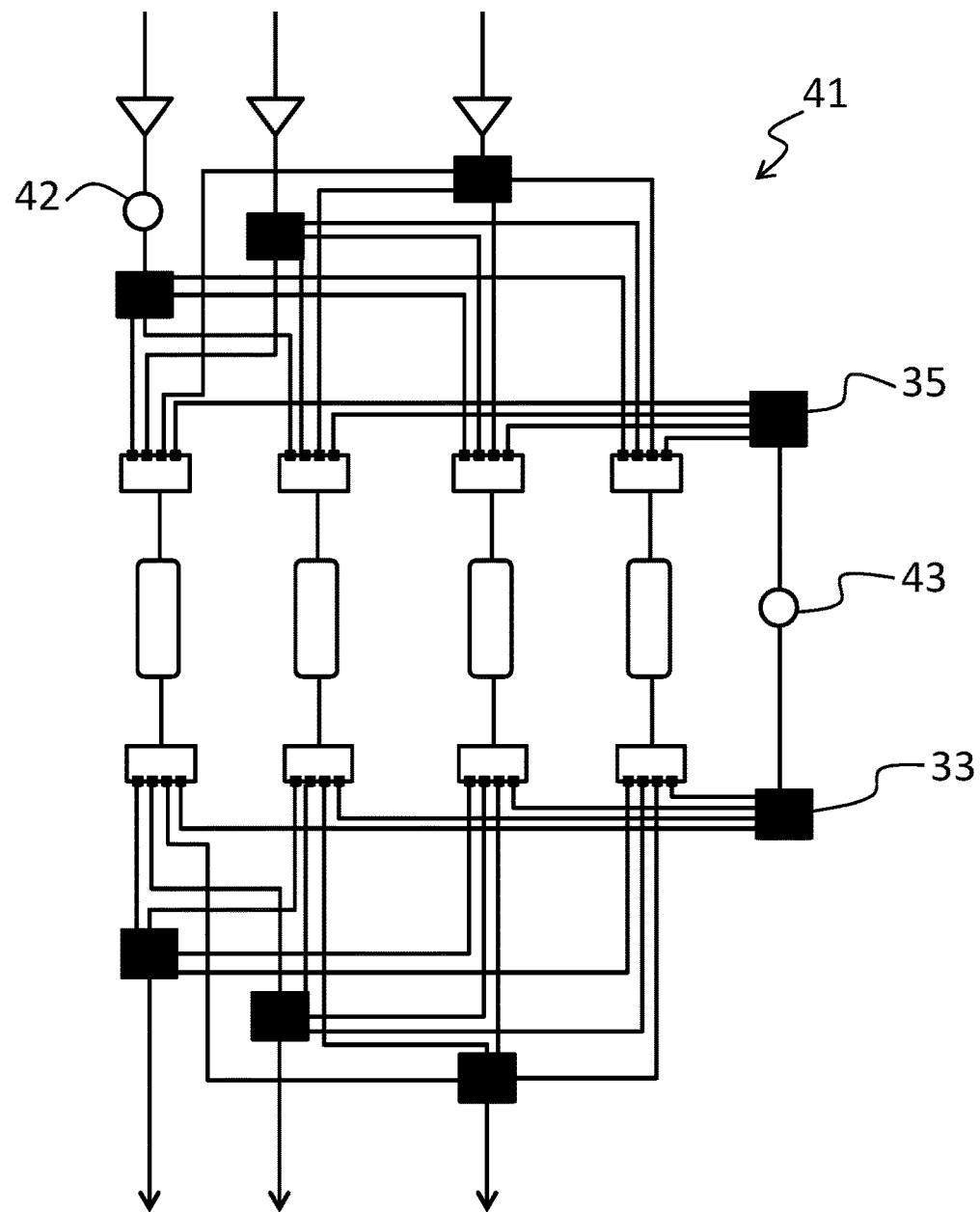
FIG. 3a shows schematically a chromatography system according to one embodiment of the invention.

FIG. 3a shows schematically a chromatography system 41 according to another embodiment of the invention. Most parts are the same as in the embodiment shown in FIG. 2a and will not be described further here. They are named and numbered the same as in FIG. 2a. The difference is that in this embodiment the first, second, third and fourth detectors 32a,b,c,d of FIG. 2a has been replaced by one single feed recirculation detector 43. This feed recirculation detector 43 is adapted to detect an effluent signal being representative of the composition of the feed recirculation in the same way as described above and this could be for example a UV detector or any of the other examples mentioned above. This feed recirculation detector 43 is positioned between the feed recirculation flow uniter 33 and the feed recirculation flow splitter 35. Hereby the number of needed detectors has been decreased by three. This is of course suitable from a cost perspective. However, one additional detector 42 can suitably be provided in this embodiment for the elution.

Figure 3B:
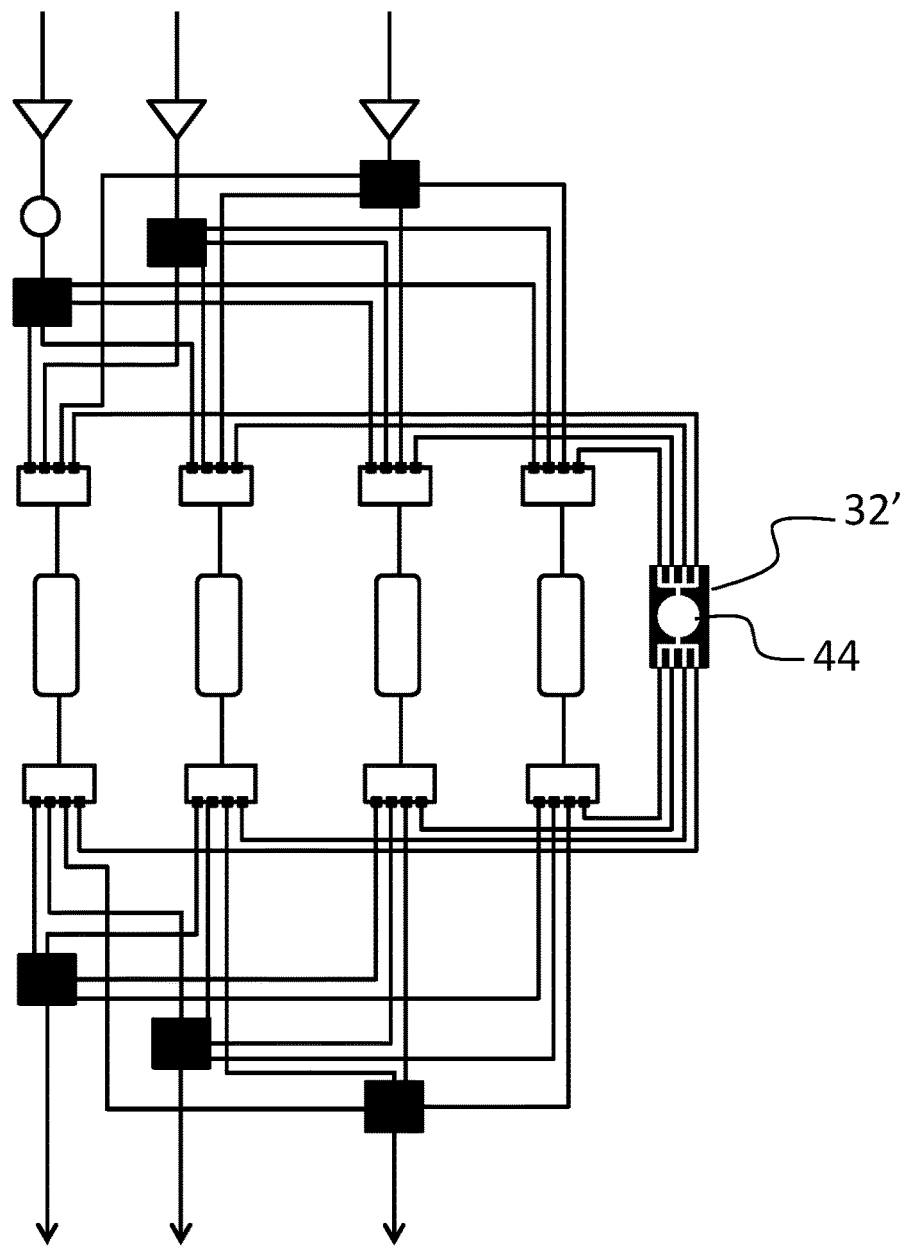
FIG. 3b shows schematically a chromatography system according to one embodiment of the invention.

FIG. 3b shows another embodiment of the invention which is similar to the embodiment shown in FIG. 2b. One feed recirculation means 32' is shown. However in this embodiment the four detectors 32a,b,c,d of FIG. 2b has been replaced by one feed recirculation detector 44 provided inside the feed recirculation means 32'.

Figure 3C:
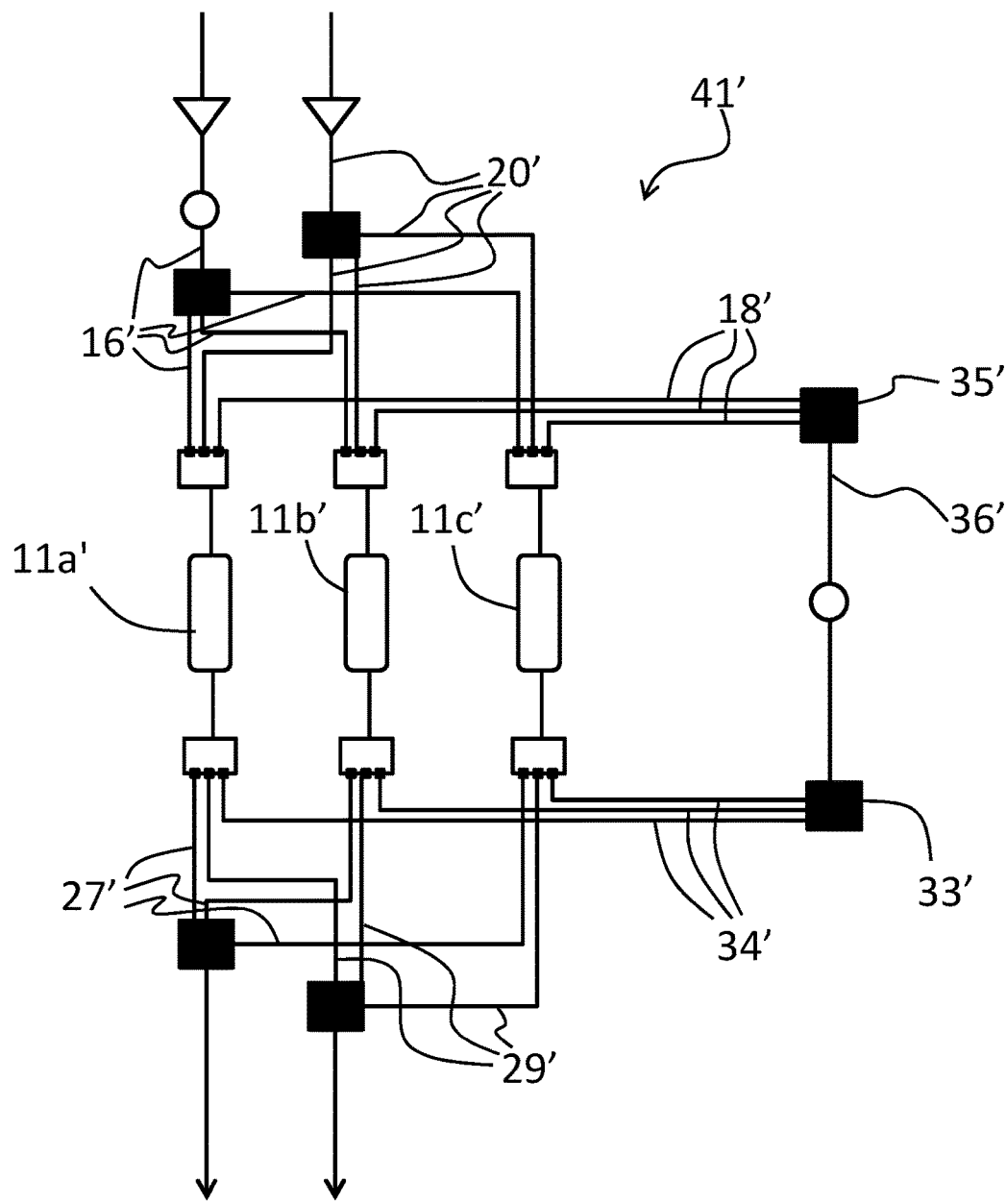
FIG. 3c shows a similar system as shown in FIG. 3a but with only three columns.

FIG. 3c shows a similar system 41' as shown in FIG. 3a but with only three columns 11a', 11b', 11c'. Feed recirculation is combined for all columns also in this system. First outflows 34' from the columns are combined in a flow uniter 33' which is connected through a feed recirculation flow path 36' to a flow splitter 35'. Second inflows 18' is provided to all the columns from the flow splitter 35'. The difference from a four column system is that only three different inflows are provided where the first inflow 16' is feed, the second inflow 18' is feed recirculation and the third inflow 20' is alternating between elution and regeneration. In the same way only three outflows are provided in this system: a first outflow 34' is the feed recirculation, a second outflow 27' is feed outlet and a third outflow 29' is combined regeneration outlet and elution outlet.

Figure 3D:
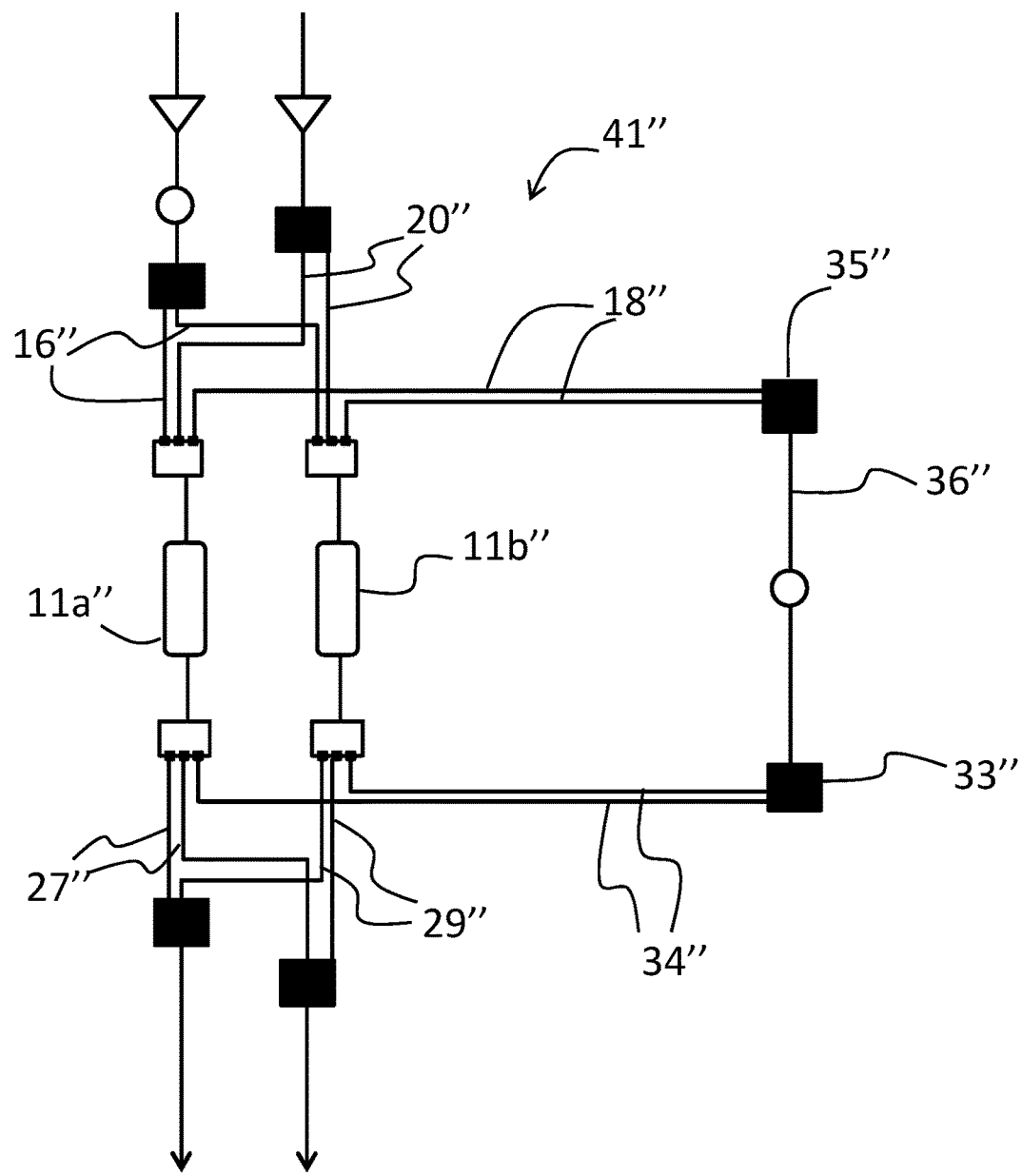
FIG. 3d shows a similar system as shown in FIG. 3a but with only two columns.

FIG. 3*d* shows a similar system 41" as shown in FIG. 3*a* but with only two columns 11*a*", 11*b*". Feed recirculation is combined for all columns also in this system. First outflows 34" from the columns are combined in a flow uniter 33" which is connected through a feed recirculation flow path 36" to a flow splitter 35". Second inflows 18" is provided to all the columns from the flow splitter 35". The difference from a four column system is that only three different inflows are provided where the first inflow 16" is feed, the second inflow 18" is feed recirculation and the third inflow 20" is alternating between elution and regeneration. In the same way only three outflows are provided in this system: a first outflow 34" is the feed recirculation, a second outflow 27" is feed outlet and a third outflow 29" is combined regeneration outlet and elution outlet. The difference from a three columns system as shown in FIG. 3*c* is that the feed is separated into two stages. In the first stage of the feed no recirculation is provided and the outlet from the feed column (let's say the first column 11*a*" in this example) is provided to the second outflow 27". At the same time both elution and regeneration is provided to the second column 11*b*" (from third inflow 20"). When elution and regeneration is ready on the second column 11*b*" the recirculation is started and recirculation flow (from second inflow 18") is provided to the second column 11*b*" while feed is continued to be provided to the first column 11*a*".

Figure 4A:
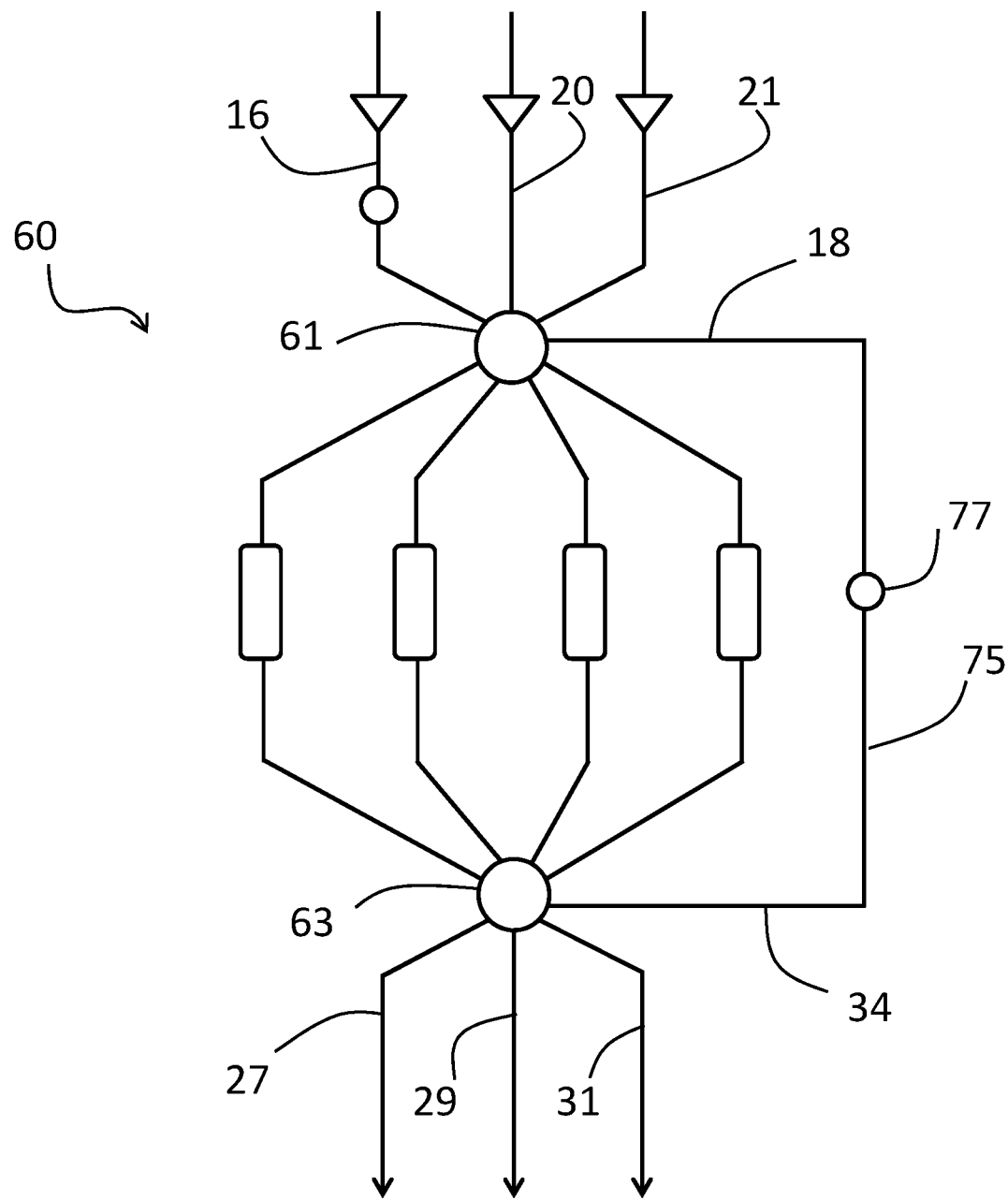
FIG. 4a shows schematically a chromatography system according to one embodiment of the invention.

FIG. 4*a* shows schematically a chromatography system 60 according to one embodiment of the invention. Also in this embodiment four columns 11*a*, 11*b*, 11*c*, 11*d* are shown. However the four inlet valves 13*a,b,c,d* of the previous embodiments have been exchanged to one single column inlet rotary valve 61. This column inlet rotary valve 61 is connected to the inlets of all the columns in the system and furthermore to a first inflow 16 (as before representing feed), a second inflow 18 (as before representing feed recirculation), a third inflow 20 (representing regeneration buffer) and a fourth inflow 21 (representing elution buffer). The four outlet valves 15*a,b,c,d* of the previous embodiments are here replaced by one single column outlet rotary valve 63. This column outlet rotary valve 63 is connected to the outlets of all the columns in the system and furthermore to a first outflow 34 (as before representing feed recirculation), a second outflow 27 (representing feed outlet), a third outflow 29 (representing regeneration outlet) and a fourth outflow 31 (representing elution outlet). A feed recirculation flow path 75 is provided between the column inlet rotary valve 61 and the column outlet rotary valve 63. All feed recirculation from load column to secondary load column will be transferred through this feed recirculation flow path 75. A detector 77 is provided in the feed recirculation flow path 75. As above this detector is adapted to detect an effluent signal being representative of the composition of the feed recirculation flowing through the feed recirculation flow path 75. In one embodiment the detector is a UV detector, i.e. measuring the UV absorbance of the sample. Other possible types of detectors are measuring pH, conductivity, light scattering, fluorescence, IR or visible light. This definition of detector will be the same throughout the description.

Figure 4B:
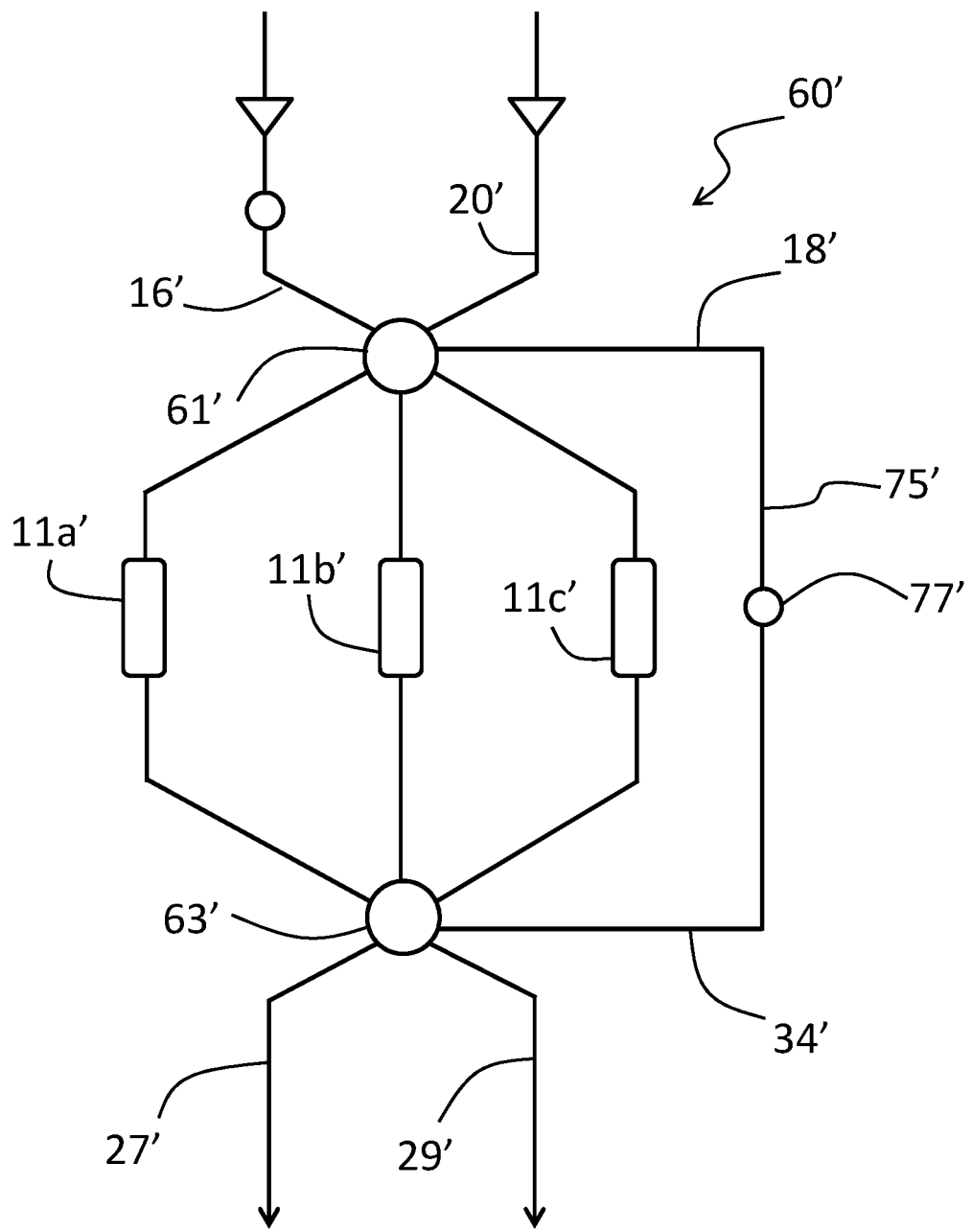
FIG. 4b shows schematically a chromatography system with three columns according to one embodiment of the invention.

FIG. 4*b* shows schematically a chromatography system 60' according to one embodiment of the invention. In this embodiment three columns 11*a*', 11*b*', 11*c*' are connected in a simulated moving bed system. A column inlet rotary valve 61' is connected to the inlets of the columns in the system. This column inlet rotary valve 61' is connected to the inlets of all the columns in the system and furthermore to a first inflow 16' (in this embodiment representing feed), a second inflow 18' (in this embodiment representing feed recirculation) and a third inflow 20' (in this embodiment representing regeneration buffer and elution buffer). A rotary valve is in this shown chromatography system provided also as a column outlet rotary valve 63'. This column outlet rotary valve 63' is connected to the outlets of all the columns in the system and furthermore to a first outflow 34' (in this embodiment representing feed recirculation), a second outflow 27' (in this embodiment representing feed outlet) and a third outflow 29' (in this embodiment representing regeneration and elution outlet). A feed recirculation flow path 75' is provided between the column inlet rotary valve 61' and the column outlet rotary valve 63'. All feed recirculation from a primary load column to a secondary load column in the simulated moving bed chromatography system will be transferred through this feed recirculation flow path 75'. A detector 77' is provided in the feed recirculation flow path 75'.

A rotary valve that can be used in the embodiments described in relation to FIGS. 4*a* and *b* comprises a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position. The stator comprises at least three primary connection ports and at least three secondary connection ports, and the rotor interconnection paths are arranged to in the different rotor positions interconnect the primary connection ports with the secondary connection ports such that all of at least three secondary connection ports can be connected one at the time to each of at least three primary connection port by rotating the rotor into the different rotor positions.

According to one embodiment of the rotary valve the interconnections of the primary connection ports with the secondary connection ports will be shifted according to a simulated moving bed process by rotating the rotor.

According to one embodiment of the rotary valve at least two of the rotor interconnection paths are partly bending grooves.

According to one embodiment of the rotary valve at least two of the rotor interconnection paths comprise one circular groove and one radial channel.

According to one embodiment of the rotary valve the circular grooves are concentrically positioned around the centre of the rotary valve and have different radius corresponding to the different radius at which the secondary valve orifices are provided and the radial channels are provided reaching out from their respective circular grooves to the positions of the primary valve orifices.

According to one embodiment of the rotary valve extra primary connection ports and valve orifices are provided in the stator in order to allow column bypass and/or additional set up of columns.

The chromatography system as described in relation to FIGS. 4*a* and *b* can be defined as a chromatography system comprising at least three chromatography columns 11a, 11b, 11c, 11d, said system further comprising:
- a column inlet rotary valve 61 connected to the inlets of at least three columns in the system and to at least three inflows and
- a column outlet rotary valve 63 connected to the outlets of at least three columns in the system and to at least three outflows, and
- a feed recirculation flow path 75 in which feed recirculation from the outlet of the column presently serving as primary load column in a chromatography process to the inlet of the column presently serving as secondary load column is transferred, wherein said feed recirculation flow path transfers the feed recirculation from all the columns in the system serving as primary load columns and wherein said feed recirculation flow path is connected to the inlets and outlets of the columns through the column inlet and column outlet rotary valves.

The system can in one embodiment further be defined as a chromatography system, wherein inlets of said chromatography columns are connected one to each of said primary connection ports of the inlet rotary valve 61 and outlets of said chromatography columns are connected one to each of said primary connection ports of the outlet rotary valve 63 and said inflows are connected one to each of said secondary connection ports of the inlet rotary valve 61 and said outflows are connected one to each of said secondary connection ports of the outlet rotary valve 63 and wherein said rotor interconnection paths are provided such that each of at least three inflows can be connected one at the time with each of at least three column inlets through the inlet rotary valve 61 and each of at least three outflows can be connected one at the time with each of at least three column outlets through the outlet rotary valve 63 and by rotating the rotors the inflows to the column inlets and the outflows to the column outlets will be shifted according to a simulated moving bed process.

Figure 5A:
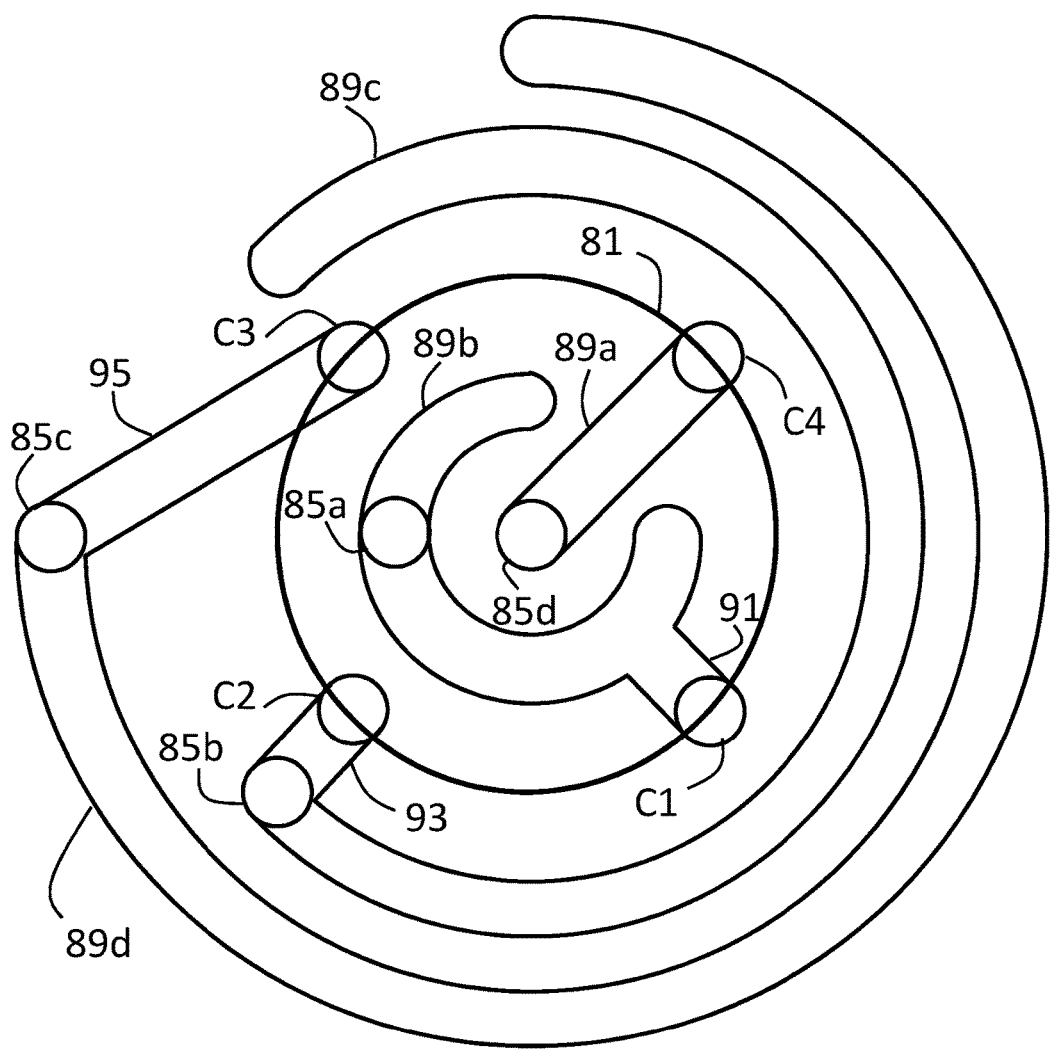
Figure 5B:
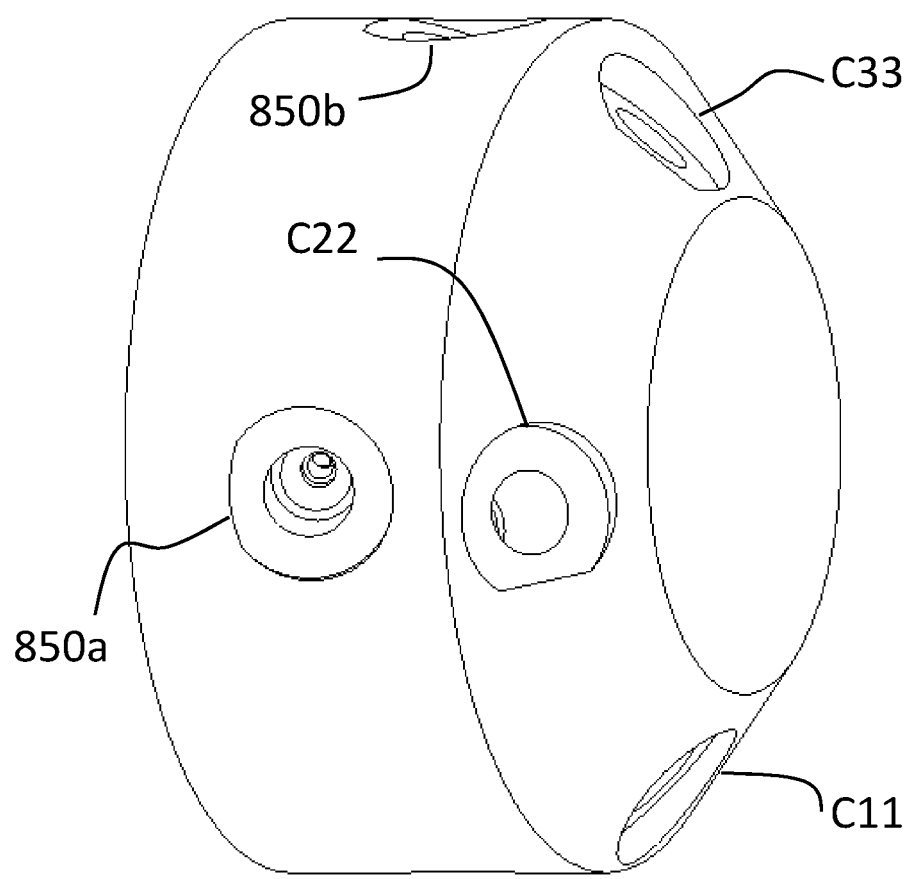
FIG. 5b shows an outside of a stator with connection ports.

FIG. 5a shows a possible design of a column inlet or outlet rotary valve 61, 63 that can be used in the embodiment of the invention shown in FIG. 4a. A rotary valve comprises a stator with an inner stator face, and a rotor with an inner rotor face arranged in sealing contact with the inner stator face. The rotor is rotatably movable to a plurality of rotor positions about a rotational axis relative to the inner stator face. The stator comprises a plurality of connection ports each being in fluidic contact with a corresponding valve orifice at the inner stator face and the rotor comprises two or more interconnection paths for selective fluidic interconnection of said valve orifices with respect to the rotor position. In FIG. 5a the valve orifices on the inner stator face and the interconnecting paths on the rotor are shown in the same view. In FIG. 5b connection ports on the outside of a stator is shown. However, these connection ports can be positioned in any wanted way. In this embodiment of the rotary valve used in FIG. 4a the stator comprises four primary valve orifices C1, C2, C3, C4 each being in fluidic contact with a corresponding primary connection port (only three can be seen in the view shown in FIG. 5b, C11, C22, C33) of the stator. In this example the primary connection ports are connected to columns in the system. The stator comprises further four secondary valve orifices 85a, 85b, 85c, 85d each being in fluidic contact with a corresponding secondary connection port of the stator (only two can be seen in the view shown in FIG. 5b, 850a, 850b). In this example the secondary connection ports are connected to inflows (for inlet rotary valve) or outflows (for outlet rotary valve) in the system shown in FIG. 4a. The interconnection paths in the rotor are arranged to, in the different rotor positions interconnect the primary valve orifices C1, C2, C3, C4 with the secondary valve orifices 85a, 85b, 85c, 85d such that all secondary valve orifices can be connected one at the time to each primary valve orifice by rotating the rotor into the different rotor positions.

In FIG. 5a stator valve orifices are shown by circles. There are four primary valve orifices denoted C1, C2, C3 and C4. The corresponding primary connection ports of the stator are in this embodiment connections to the columns in the system. Furthermore, there are four secondary valve orifices, a first secondary valve orifice 85a, a second secondary valve orifice 85b, a third secondary valve orifice 85c and a fourth secondary valve orifice 85d. For an inlet rotary valve 61 the first secondary valve orifice 85a will in the embodiment shown in FIG. 4a be connected to feed through a corresponding first secondary connection port in the stator, the second secondary valve orifice 85b will be connected to feed recirculation through a corresponding second secondary connection port in the stator, the third secondary valve orifice 85c will be connected to regeneration through a corresponding third secondary connection port in the stator and the fourth secondary valve orifice 85d will be connected to elution through a corresponding fourth secondary connection port in the stator. If the rotary valve is used as outlet rotary valve 63 the first secondary valve orifice 85a will be connected to feed recirculation as discussed above through a first secondary connection port in the stator, the second secondary valve orifice 85b will be connected to feed outlet through a second secondary connection port in the stator, the third secondary valve orifice 85c will be connected to regeneration outlet through a third secondary connection port of the stator and the fourth secondary valve orifice 85d will be connected to elution outlet as discussed above through a fourth secondary connection port of the stator.

However, the order and organisation and naming of these secondary valve orifices could be varied as long as the simulated moving bed process is followed from rotation of the rotor of the rotation valve. In the rotor of the rotary valve there are in this embodiment provided rotor interconnection paths as grooves. In this embodiment three of these rotor interconnection paths are provided partly along a part of a circle. The rotor interconnection paths are arranged such that each one of the primary valve orifices C1, C2, C3, C4 is connected to one each of the secondary valve orifices 85a,b,c,d in each rotational position of the rotary valve. By rotating the rotor of the rotary valve into four different positions the connections of inflows/outflows (FIG. 4a) to the columns will be shifted according to the simulated moving bed process. This is also shown in FIGS. 6a-6d. I.e.:
- In a first rotational position (FIG. 6a) of the rotary valve the first primary valve orifice C1 is connected to the first secondary valve orifice 85a, the second primary valve orifice C2 is connected to the second secondary valve orifice 85b, the third primary valve orifice C3 is connected to the third secondary valve orifice 85c and the fourth primary valve orifice C4 is connected to the fourth secondary valve orifice 85d.
- In a second rotational position (FIG. 6b) of the rotary valve the first primary valve orifice C1 is connected to the fourth secondary valve orifice 85d, the second primary valve orifice C2 is connected to the first secondary valve orifice 85a, the third primary valve orifice C3 is connected to the second secondary valve orifice 85b and the fourth primary valve orifice C4 is connected to the third secondary valve orifice 85c.

In a third rotational position (FIG. 6c) of the rotary valve the first primary valve orifice C1 is connected to the third secondary valve orifice 85c, the second primary valve orifice C2 is connected to the fourth secondary valve orifice 85d, the third primary valve orifice C3 is connected to the first secondary valve orifice 85a and the fourth primary valve orifice C4 is connected to the second secondary valve orifice 85b.

In a fourth rotational position (FIG. 6d) of the rotary valve the first primary valve orifice C1 is connected to the second secondary valve orifice 85b, the second primary valve orifice C2 is connected to the third secondary valve orifice 85c, the third primary valve orifice C3 is connected to the fourth secondary valve orifice 85d and the fourth primary valve orifice C4 is connected to the first secondary valve orifice 85a.

In this shown embodiment of the invention the four primary valve orifices C1, C2, C3, C4 are provided with equal distance from each other around a primary circle 81 on the stator. The four secondary valve orifices 85a,b,c,d are positioned on the inner stator face such that they in different rotor positions can connect to each one of the four primary valve orifices in an order suitable for the simulated moving bed process as described above. In the embodiment shown in FIGS. 5a and 6 the secondary valve orifices positions for two of these are provided inside the primary circle 81 on which the primary valve orifices are provided and one of these in the centre of the stator. In this example it is shown that the fourth secondary valve orifice 85d position is provided in the centre of the stator and the first secondary valve orifice 85a position is provided between the centre and the primary circle 81. The other two secondary valve orifices, here named second secondary valve orifice 85b and third secondary valve orifice 85c, are provided at different radius from the centre outside the primary circle 81 and also separated in another direction. The design of the rotor interconnection paths in the rotor should then be provided such that all four primary valve orifices can be connected to each one of the secondary valve orifices 85a,b,c,d in different rotor positions. To achieve this at least three of the rotor interconnection paths need to comprise parts that are bent. In this embodiment a first rotor interconnection path 89a is provided such that it in all rotor positions connects the fourth secondary valve orifice 85d with one of the primary valve orifices C1, C2, C3, C4. A second rotor interconnection path 89b is provided such that it in all rotor positions connects the first secondary valve orifice 85a with one of the primary valve orifices C1, C2, C3, C4. To achieve this the second rotor interconnection path 89b is provided partly as a bended groove along a part of a circle inside the primary circle 81. Furthermore, the second rotor interconnection path 89b comprises an extending part 91 extending out form the bended part to the position of the primary circle 81 in order to be able to connect the first secondary valve orifice 85a with all the primary valve orifices C1, C2, C3, C4, one in each rotor position. A third rotor interconnection path 89c is provided such that it in all rotor positions connects the second secondary valve orifice 85b with one of the primary valve orifices C1, C2, C3, C4. To achieve this the third rotor interconnection path 89c is provided partly as a bended groove along a part of a circle outside the primary circle 81. Furthermore, the third rotor interconnection path 89c comprises an extending part 93 extending inwardly form the bended part to the position of the primary circle 81 in order to be able to connect the second secondary valve orifice 85b with all the primary valve orifices C1, C2, C3, C4, one in each rotor position. A fourth rotor interconnection path 89d is provided such that it in all rotor positions connects the third secondary valve orifice 85c with one of the primary valve orifices C1, C2, C3, C4. To achieve this the fourth rotor interconnection path 89d is provided partly as a bended groove along a part of a circle outside the primary circle 81 and outside the third rotor interconnection path 89c. Furthermore, the fourth rotor interconnection path 89d comprises an extending part 95 extending inwardly form the bended part to the position of the primary circle 81 in order to be able to connect the third secondary valve orifice 85c with all the primary valve orifices C1, C2, C3, C4, one in each rotor position. This extending part 95 needs to be bended or declined for allowing all connections properly. The functions and positions of the different stator valve orifice can be varied as long as the simulated moving bed process as described above is achieved through the different rotor positions.

With an inlet rotary valve and an outlet rotary valve as shown in FIG. 5a the simulated moving bed system 60 shown in FIG. 4a can be operated and feed recirculation can be provided through one single feed recirculation flow path 75. This feed recirculation flow path 75 is therefore connected to the second secondary valve orifice 85b of the inlet rotary valve 61 and to the first secondary valve orifice 85a of the outlet rotary valve 63.

Figure 5C:
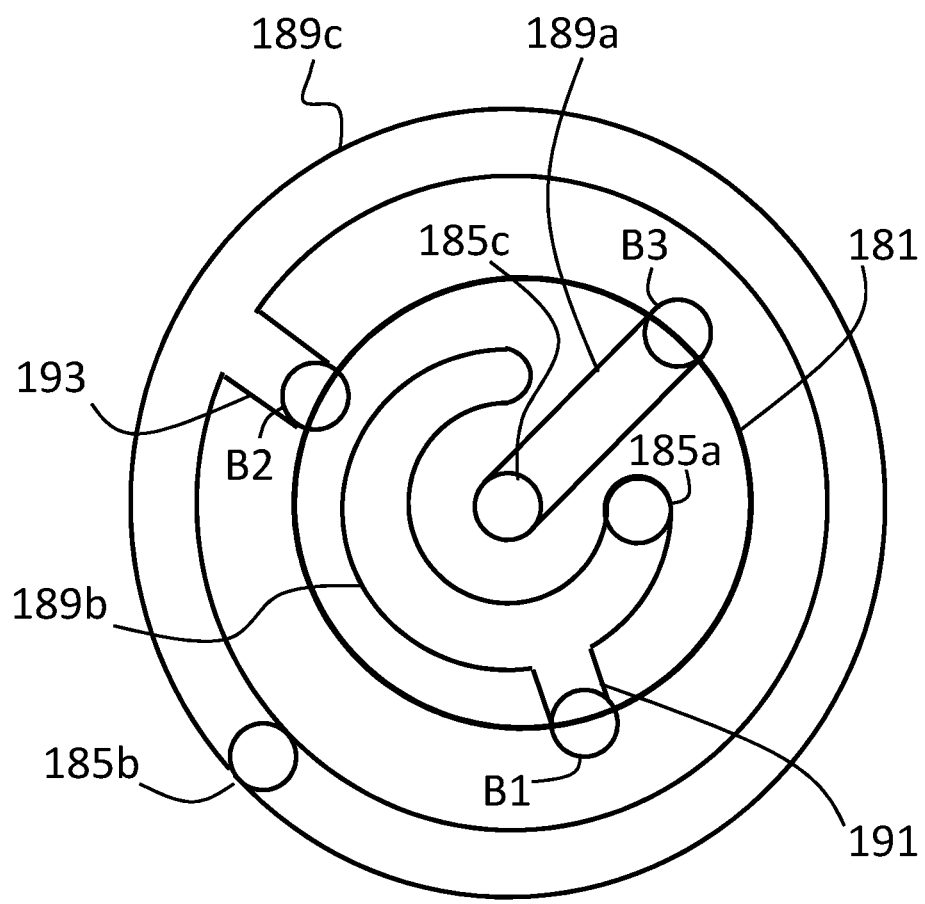
FIG. 5c shows a rotary valve that can be used in the chromatography system of FIG. 4b.
Figure 6A:
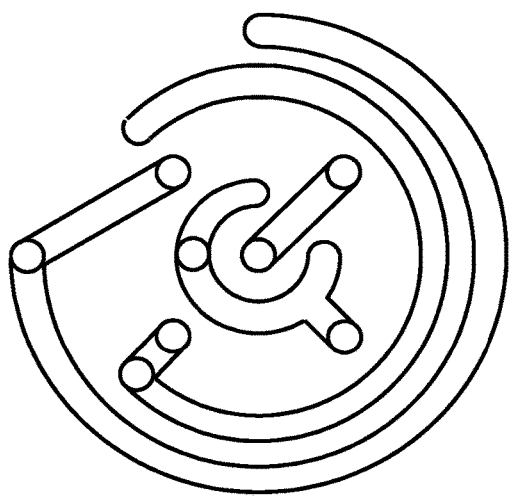
Figure 6B:
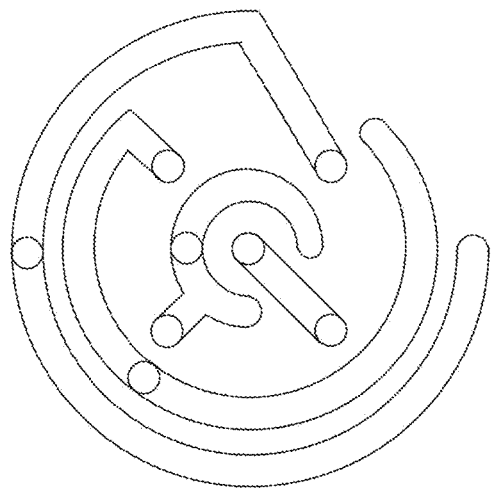
Figure 6C:
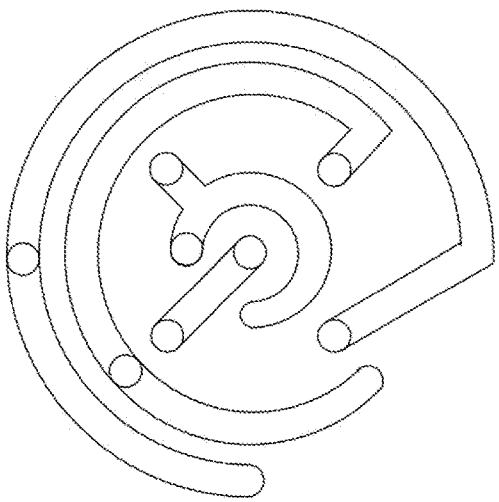
Figure 6D:
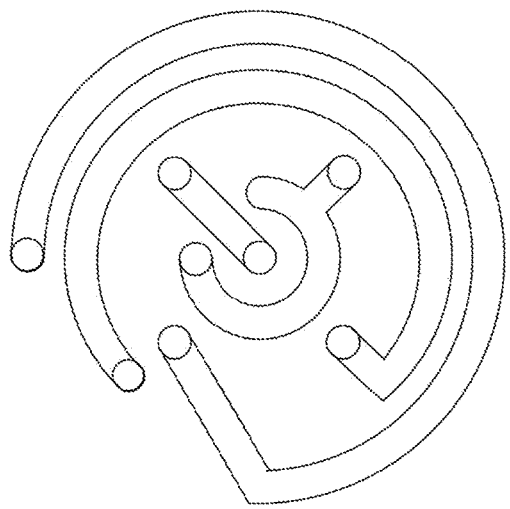

FIG. 5c shows a possible design of a column inlet or outlet rotary valve 61', 63' that can be used in the embodiment of the invention shown in FIG. 4b. In FIG. 5c the valve orifices on the inner stator face and the interconnecting paths on the rotor are shown in the same view. In this embodiment of the rotary valve used in FIG. 4b the stator comprises three primary valve orifices B1, B2, B3 each being in fluidic contact with a corresponding primary connection port of the stator. In this example the primary connection ports are connected to columns in the system. The stator comprises further three secondary valve orifices 185a, 185b, 185c each being in fluidic contact with a corresponding secondary connection port of the stator. In this example the secondary connection ports are connected to inflows (for inlet rotary valve) or outflows (for outlet rotary valve) in the system shown in FIG. 4b. The interconnection paths in the rotor are arranged to, in the different rotor positions interconnect the primary valve orifices B1, B2, B3 with the secondary valve orifices 185a, 185b, 185c such that all secondary valve orifices can be connected one at the time to each primary valve orifice by rotating the rotor into the different rotor positions.

In FIG. 5c stator valve orifices are shown by circles. For an inlet rotary valve 61' the first secondary valve orifice 185a will in the embodiment shown in FIG. 4b be connected to feed through a corresponding first secondary connection port in the stator, the second secondary valve orifice 185b will be connected to feed recirculation through a corresponding second secondary connection port in the stator, the third secondary valve orifice 185c will be connected to regeneration and to elution through a corresponding third secondary connection port in the stator. If the rotary valve is used as outlet rotary valve 63' the first secondary valve orifice 185a will be connected to feed recirculation as discussed above through a first secondary connection port in the stator, the second secondary valve orifice 185b will be connected to feed outlet through a second secondary connection port in the stator, the third secondary valve orifice 185c will be connected to regeneration and to elution outlet through a third secondary connection port of the stator as discussed above.

However, the order and organisation and naming of these secondary valve orifices could be varied as long as the simulated moving bed process is followed from rotation of the rotor of the rotary valve. In the rotor of the rotary valve there are in this embodiment provided rotor interconnection paths as grooves. In this embodiment two of these rotor interconnection paths are provided partly along at least a part of a circle. The rotor interconnection paths are arranged such that each one of the primary valve orifices B1, B2, B3 is connected to one each of the secondary valve orifices 185a,b,c in each rotational position of the rotary valve. By rotating the rotor of the rotary valve into three different positions the connections of inflows/outflows (FIG. 4b) to the columns will be shifted according to the simulated moving bed process.

In this shown embodiment of the invention the three primary valve orifices B1, B2, B3 are provided with equal distance from each other around a primary circle 181 on the stator. The three secondary valve orifices 185a,b,c are positioned on the inner stator face such that they in different rotor positions can connect to each one of the three primary valve orifices in an order suitable for the simulated moving bed process as described above. In the embodiment shown in FIG. 5c the secondary valve orifices positions for two of these are provided inside the primary circle 181 on which the primary valve orifices are provided and one of these in the centre of the stator. In this example it is shown that the third secondary valve orifice 185c position is provided in the centre of the stator and the first secondary valve orifice 185a position is provided between the centre and the primary circle 181. The last secondary valve orifice, here named second secondary valve orifice 185b, is provided outside the primary circle 181. The design of the rotor interconnection paths in the rotor should then be provided such that all three primary valve orifices can be connected to each one of the secondary valve orifices 185a,b,c in different rotor positions. To achieve this at least two of the rotor interconnection paths need to comprise parts that are bent. In this embodiment a first rotor interconnection path 189a is provided such that it in all rotor positions connects the third secondary valve orifice 185c with one of the primary valve orifices B1, B2, B3. A second rotor interconnection path 189b is provided such that it in all rotor positions connects the first secondary valve orifice 185a with one of the primary valve orifices B1, B2, B3. To achieve this the second rotor interconnection path 189b is provided partly as a bended groove along a part of a circle inside the primary circle 181. Furthermore, the second rotor interconnection path 189b comprises an extending part 191 extending out form the bended part to the position of the primary circle 181 in order to be able to connect the first secondary valve orifice 185a with all the primary valve orifices B1, B2, B3 one in each rotor position. A third rotor interconnection path 189c is provided such that it in all rotor positions connects the second secondary valve orifice 185b with one of the primary valve orifices B1, B2, B3. To achieve this the third rotor interconnection path 189c is in this embodiment provided as a complete circle outside the primary circle 181. Furthermore, the third rotor interconnection path 189c comprises an extending part 193 extending inwardly form the bended part to the position of the primary circle 181 in order to be able to connect the second secondary valve orifice 185b with all the primary valve orifices B1, B2, B3 one in each rotor position. The functions and positions of the different stator valve orifices can be varied as long as the simulated moving bed process as described above is achieved through the different rotor positions.

With an inlet rotary valve and an outlet rotary valve as shown in FIG. 5c the simulated moving bed system 60' shown in FIG. 4b can be operated and feed recirculation can be provided through one single feed recirculation flow path 75'. This feed recirculation flow path 75' is therefore connected to the second secondary valve orifice 185b of the inlet rotary valve 61' and to the first secondary valve orifice 185a of the outlet rotary valve 63'.

Figure 7:
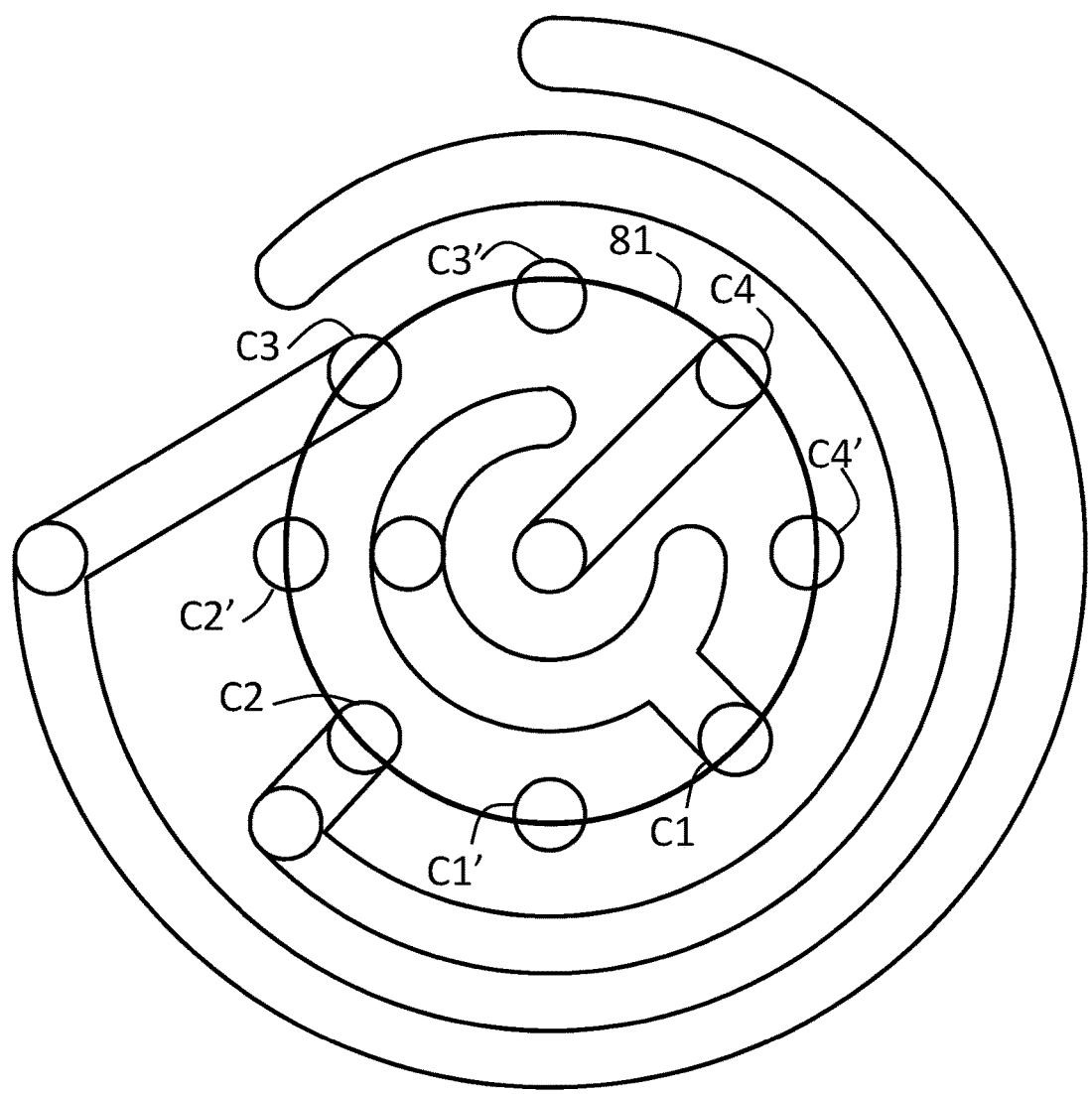

FIG. 7 shows the design of another embodiment of a rotary valve that can be used in the embodiment shown in FIG. 4a. In this embodiment the function of column bypass has been included. To provide this four extra primary valve orifices C1', C2', C3', C4' are provided in between the primary valve orifices C1, C2, C3, C4 on the primary circle 81. Flow connections can be provided between the inlet and outlet valves such that fluid can be pumped through the system without entering the columns. This can be used for system wash. The design of the rotor and stator is beside this much the same as described for the previous embodiments and will not be described further here.

Figure 8:
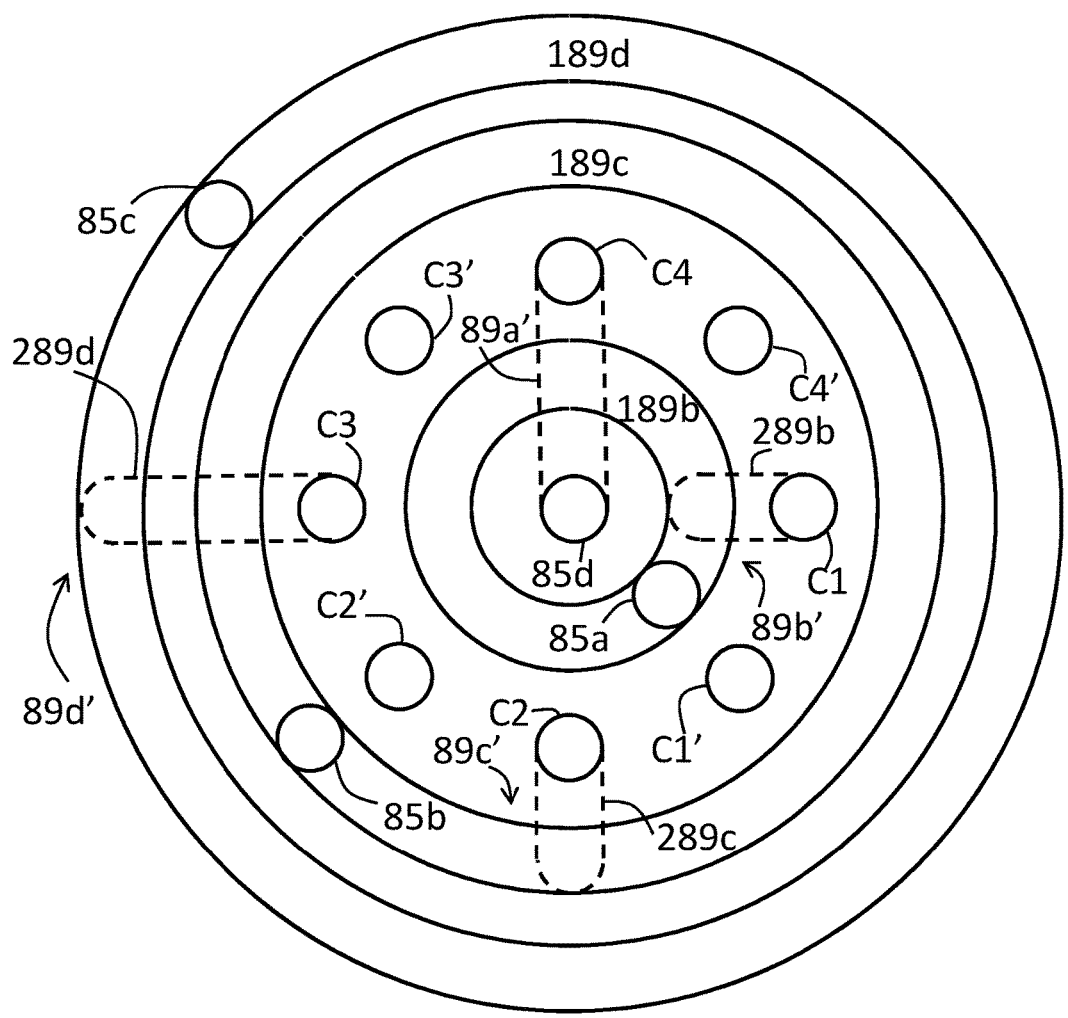

FIG. 8 shows another embodiment of the rotary valve shown in FIGS. 5 and 7. This embodiment could be provided with or without the bypass function as described in relation to FIG. 7. Here the four extra primary valve orifices C1', C2', C3' and C4' are shown but they could also be omitted. Four primary valve orifices C1, C2, C3 and C4 are shown in this embodiment. They are provided with equal distances around a primary circle 81 in the same way as described for the embodiment shown in FIG. 5a. The secondary valve orifices 85a, 85b, 85c, 85d of the stator are also provided at the same positions as in the embodiment described with reference to FIG. 5a. The difference is that the rotor interconnection paths have been divided into circular grooves on the inner rotor face and radial channels which are drilled within the rotor. Hereby the circular grooves will not interfere with the radial channels and the circular grooves can be provided as complete circles. In more detail a first rotor interconnection path 89a' is provided as a first radial channel connecting the fourth primary valve orifice C4 and the fourth secondary valve orifice 85d. This channel is provided below the surface of the rotor and below the bottom of the circular grooves which will be further described below. A second rotor interconnection path 89b' comprises two parts: one second circular groove part 189b which circular groove is provided inside the primary circle 81at the same distance from the center as the first secondary valve orifice 85a and one second radial channel part 289b. The second radial channel part 289b is provided from the primary circle 81 to the position of the first secondary valve orifice 85a but drilled within the rotor. A third rotor interconnection path 89c' comprises also two parts: one third circular groove part 189c which circular groove part is provided outside the primary circle 81at the same distance from the center as the second secondary valve orifice 85b and one third radial channel part 289c. The third radial channel part 289c is provided from the third circular groove part 189c to the primary circle 81 and it is drilled within the rotor. A fourth rotor interconnection path 89d' comprises also two parts: one fourth circular groove part 189d which circular groove part is provided outside the third circular groove part 189c at the same distance from the center as the third secondary valve orifice 85c and one fourth radial channel part 289d. The fourth radial channel part 289d is provided from the fourth circular groove part 189d to the primary circle 81 and it is drilled within the rotor. Hereby the circular grooves can be provided as complete circles unlike the embodiment shown in FIG. 5a. As also shown in FIG. 8 bypass can be provided also to this embodiment by including bypass column connections on the primary circle 81, C1', C2', C3', C4'.

Figure 9:
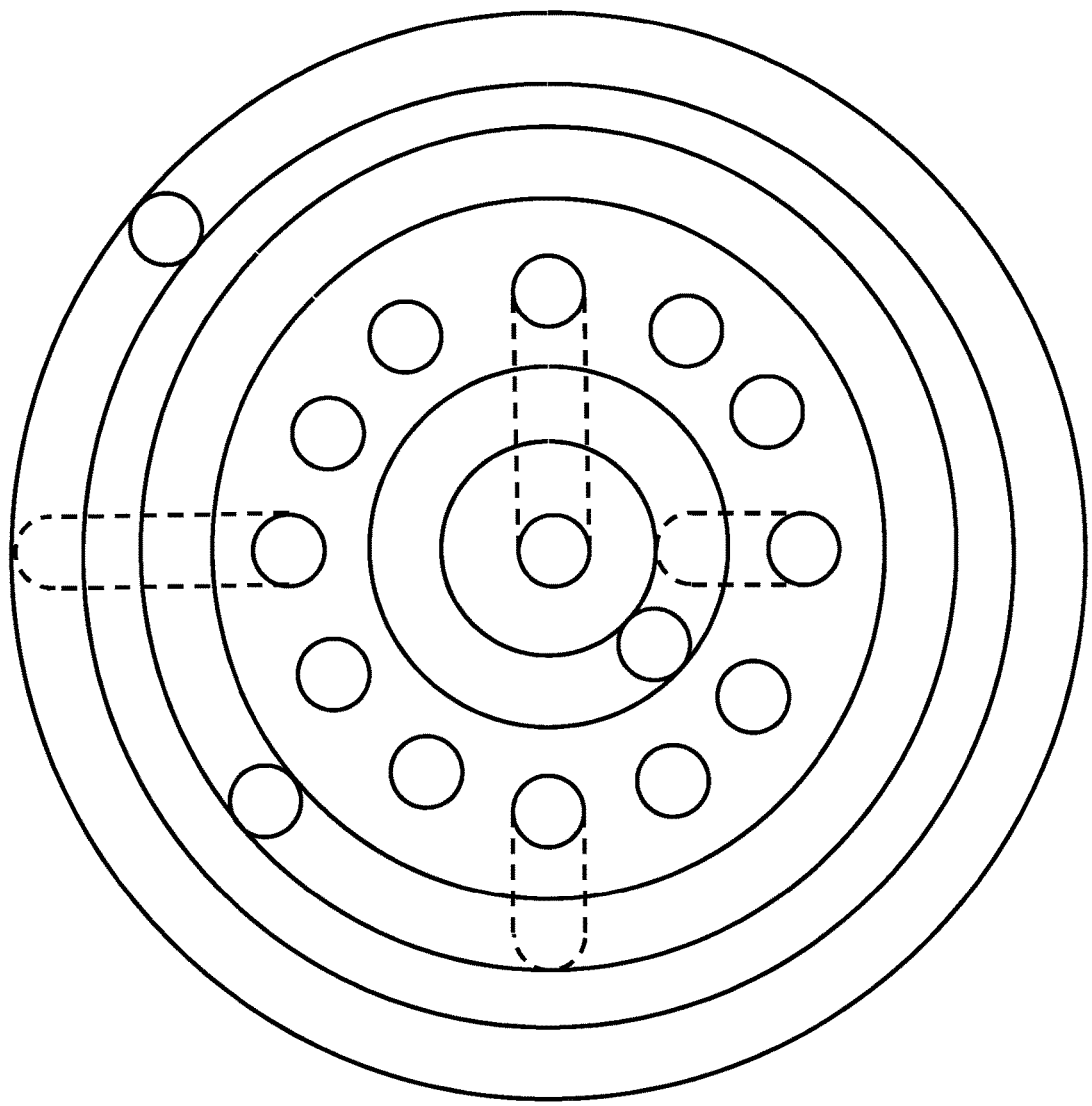

FIG. 9 shows another embodiment of the invention which embodiment is similar to the embodiment described with reference to FIG. 8. The only difference is that another set of primary valve orifices has been provided on the primary circle 81. In this way a second set of four columns can be connected to the system.

Figure 10:
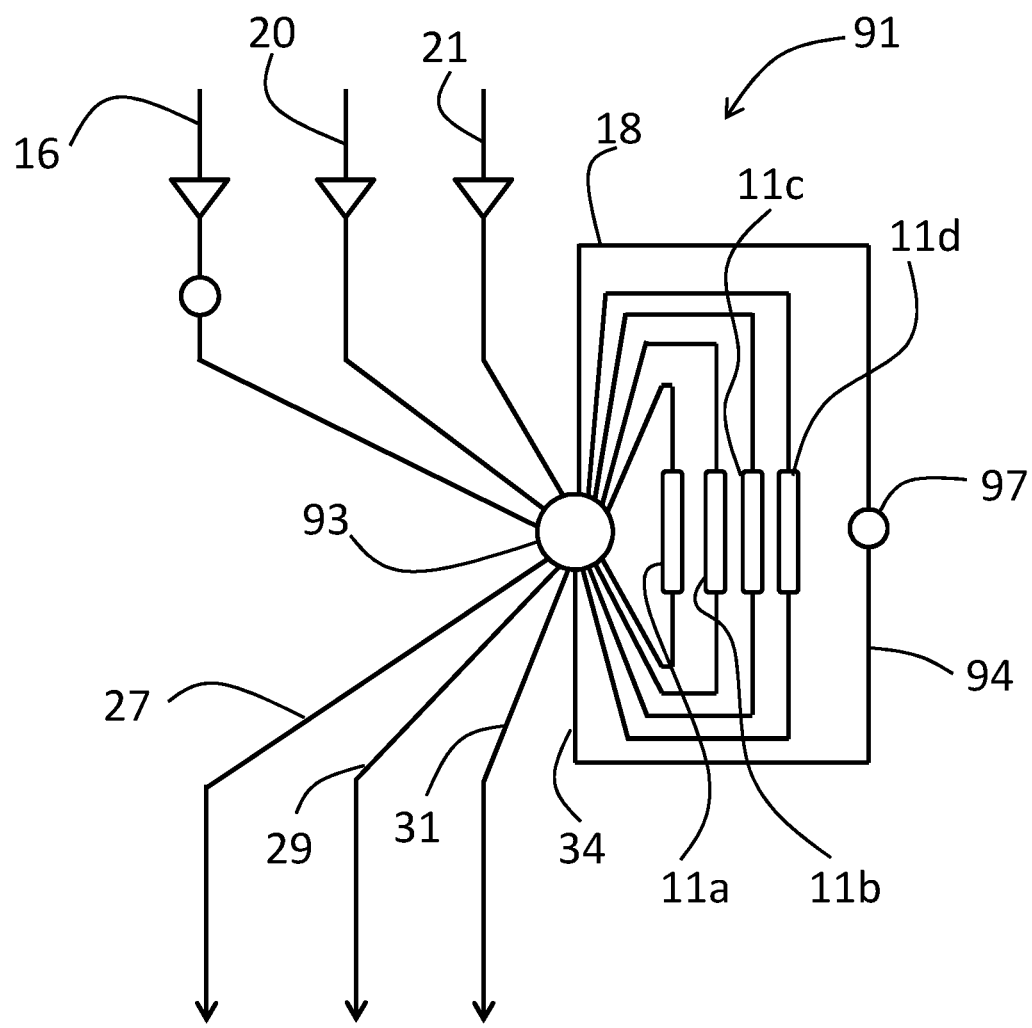
FIG. 10 shows schematically a chromatography system according to one embodiment of the invention.

FIG. 10 shows schematically a chromatography system 91 according to one embodiment of the invention. Four columns 11a,b,c,d are shown as in the other embodiments. In this embodiment only one rotary valve 93 is used for the connection to the columns instead of one column inlet rotary valve and one column outlet rotary valve as shown in the embodiment described in FIG. 4a. This rotary valve 93 is connected to both all the inlets of the four columns and to the outlets. Furthermore, it is connected to a first inflow, a second inflow, a third inflow, a fourth inflow and a first outflow, a second outflow, a third outflow and a fourth outflow according to the same principles as for the inlet and outlet rotary valves described in FIGS. 4-6. According to the invention the rotary valve 93 is connected to a feed recirculation flow path 94 enabling feed recirculation from outlet of load column to inlet of secondary load column in one single feed recirculation flow path 94 as described above. The feed recirculation flow path is as in the previous embodiments connected to the rotary valve 93 as a second inflow and as a first outflow. The feed recirculation flow path 94 also comprises a detector 97.

Figure 11:
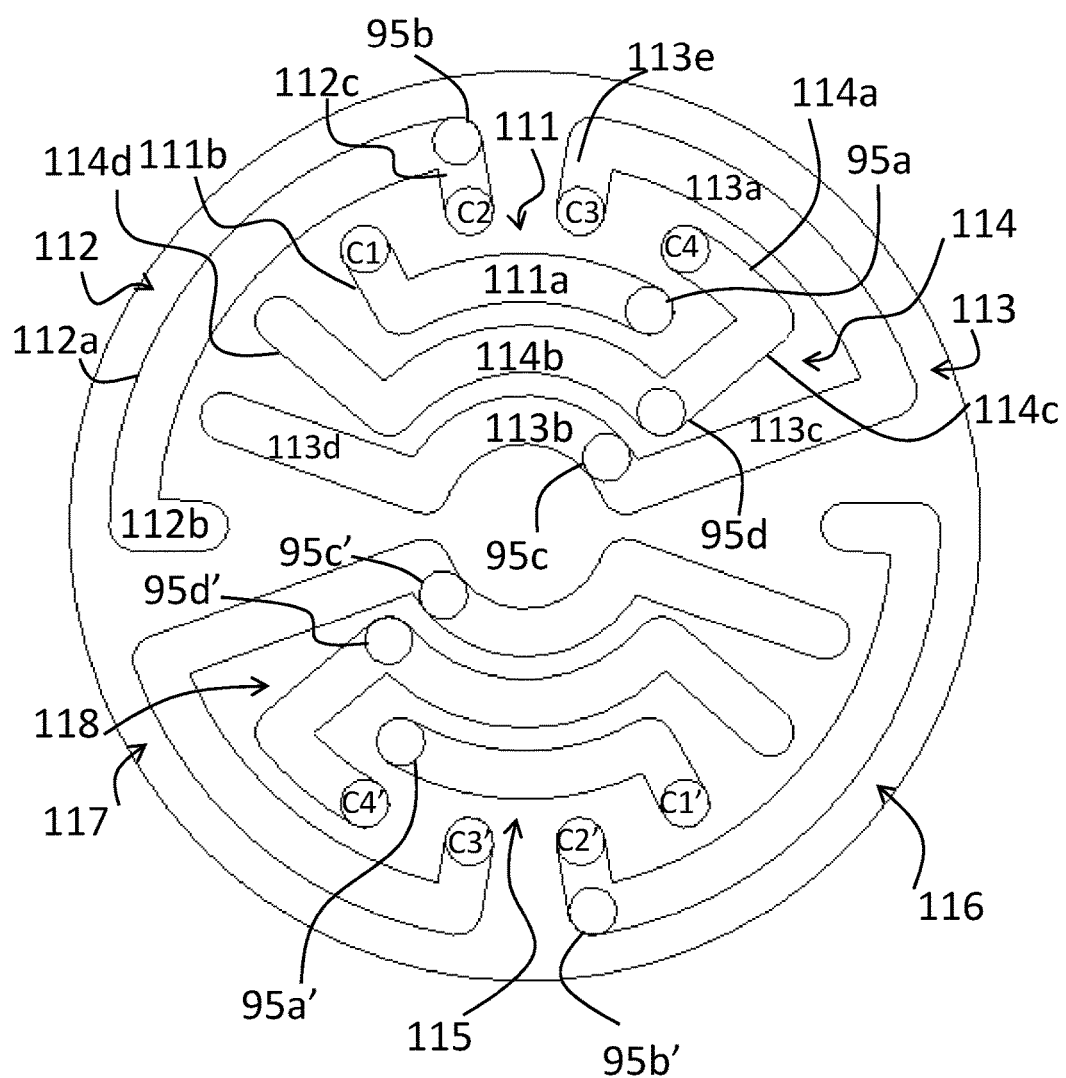
FIG. 11 shows a rotary valve according to one embodiment of the invention that can be used in the chromatography system of FIG. 10.

FIG. 11 shows the design of a rotary valve that can be used in the embodiment of the invention shown in FIG. 10. The inlet functions have been provided on one side of the rotor and stator (upper half in FIG. 11) and the outlet functions on the other side. A rotary valve comprises a stator with an inner stator face, and a rotor with an inner rotor face arranged in sealing contact with the inner stator face. The rotor is rotatably movable to a plurality of rotor positions about a rotational axis relative to the inner stator face. The stator comprises a plurality of connection ports each being in fluidic contact with a corresponding valve orifice at the inner stator face and the rotor comprises two or more interconnection paths for selective fluidic interconnection of said valve orifices with respect to the rotor position. In FIG. 11 the valve orifices on the inner stator face and the interconnecting paths on the rotor are shown in the same view. In this embodiment of the rotary valve used in FIG. 10 the stator comprises four inlet primary valve orifices C1, C2, C3, C4 each being in fluidic contact with a corresponding inlet primary connection port of the stator. These inlet primary connection ports are in this example connected to the inlets of the four columns in FIG. 10. The stator comprises further four outlet primary valve orifices C1', C2', C3', C4' each being in fluidic contact with a corresponding outlet primary connection port of the stator. These outlet primary connection ports are in this example connected to the outlets of the four columns in FIG. 10. Furthermore, the stator comprises four inlet secondary valve orifices 95a, 95b, 95c, 95d each being in fluidic contact with a corresponding inlet secondary connection port of the stator. These inlet secondary connection ports are in this example connected to the four inflows 16, 18, 20, 21 of FIG. 10. The stator comprises further four outlet secondary valve orifices 95a', 95b', 95c', 95d' each being in fluidic contact with a corresponding outlet secondary connection port of the stator. These outlet secondary connection ports are in this example connected to the four outflows 34, 27, 29, 31 of FIG. 10. The interconnection paths in the rotor are arranged to: in the different rotor positions interconnect the inlet primary valve orifices C1, C2, C3, C4 with the inlet secondary valve orifices 95a, 95b, 95c, 95d and the outlet primary valve orifices C C2', C3', C4' with the outlet secondary valve orifices 95a', 95b', 95c', 95d' such that all inlet secondary valve orifices can be connected one at the time to each inlet primary valve orifice and all outlet secondary valve orifices can be connected one at the time to each outlet primary valve orifice by rotating the rotor into the different rotor positions. Hereby all inflows 16, 18, 20, 21 in the chromatography system can be connected one at the time to each column inlet and all outflows 34, 27, 29, 31 can be connected one at the time to each column outlet by rotating the rotor into different rotor positions.

In FIG. 11 stator valve orifices are shown by circles. There are four inlet primary valve orifices denoted C1, C2, C3 and C4 and four outlet primary valve orifices denoted C1', C2', C3', C4'. These are in this embodiment connections to the columns in the system. Furthermore, there are four inlet secondary valve orifices, a first inlet secondary valve orifice 95a, a second inlet secondary valve orifice 95b, a third inlet secondary valve orifice 95c and a fourth inlet secondary valve orifice 95d. There are also four outlet secondary valve orifices, a first outlet secondary valve orifice 95a', a second outlet secondary valve orifice 95b', a third outlet secondary valve orifice 95c' and a fourth outlet secondary valve orifice 95d'. The first inlet secondary valve orifice 95a will in the embodiment shown in FIG. 10 be connected to feed, the second inlet secondary valve orifice 95b will be connected to feed recirculation, the third inlet secondary valve orifice 95c will be connected to regeneration and the fourth inlet secondary valve orifice 95d will be connected to elution. The first outlet secondary valve orifice 95a' will be connected to feed recirculation as discussed above, the second outlet secondary valve orifice 95b' will be connected to feed outlet, the third outlet secondary valve orifice 95c' will be connected to regeneration outlet and the fourth outlet secondary valve orifice 95d' will be connected to elution outlet as discussed above.

However, the order and organisation and naming of these inlet/outlet primary/secondary valve orifices could be varied as long as the simulated moving bed process is followed from rotation of the rotor of the rotation valve. In the rotor of the rotary valve there are in this embodiment provided rotor interconnection paths as grooves. In this embodiment these rotor interconnection paths are provided partly along parts of circles. The rotor interconnection paths are arranged such that each one of the inlet primary valve orifices C1, C2, C3, C4 is connected to one each of the inlet secondary valve orifices 95a,b,c,d in each rotational position of the rotary valve and such that each one of the outlet primary valve orifices C1', C2', C3', C4' is connected to one each of the outlet secondary valve orifices 95a', 95b', 95c', 95d' in each rotation position of the rotary valve. By rotating the rotor of the rotary valve into four different positions the inflow/outflow connections to the columns will be shifted according to the simulated moving bed process.

Furthermore, the rotor will in this example only be rotated over around 60 degrees. The design of the rotor interconnection paths and the position of the stator valve orifices are provided such that a rotation of the rotor at the same time as providing wanted connection shift on the inlet side provides the wanted connection shift on outlet side, i.e. if for example feed is shifted from C1 to C2 the feed recirculation should at the same time on the outlet side shift from C1 to C2 which will be the case if the rotor in FIG. 11 is rotated one step to the right. At the same time the elution buffer (fourth inflow) will be shifted to C1 on inlet side and the elution outlet (fourth outflow) to C1 on outlet side. All the grooves have bended parts and extension parts to achieve this. In more detail the inlet primary valve orifices C1, C2, C3, C4 and the outlet primary valve orifices C1', C2', C3', C4' are all provided along a primary circle 81'. The inlet primary valve orifices are provided on one half of the primary circle 81' (upper part of valve in FIG. 11) and the outlet primary valve orifices are provided on the other half of the circle (lower part of valve in FIG. 11). Four inlet rotor interconnection paths 111, 112, 113, 114 are provided on one side (inlet side, upper part in FIG. 11) of the rotary valve with purpose of connecting the inlet primary valve orifices with the inlet secondary valve orifices and four outlet rotor interconnection paths 115, 116, 117, 118 are provided on the other side of the rotary valve (outlet side, lower part in FIG. 11) with purpose of connecting outlet primary valve orifices with outlet secondary valve orifices. The first inlet rotor interconnection path 111 comprises one first bended part 111a positioned just inside the primary circle 81' and one first extension part 111b connected to the first bended part 111a and reaching out to the primary circle 81'. The first inlet secondary valve orifice 95a is provided in the first bended part 111a. The second inlet rotor interconnection path 112 comprises a second bended part 112a positioned just outside the primary circle 81' and two second extension parts 112b, 112c connected to the second bended part 112a one in each end of the second bended part 112a and both reaching out to the primary circle 81'. The third inlet rotor interconnection path 113 comprises an outer third bended part 113a and an inner third bended part 113b. The outer third bended part 113a is positioned outside the primary circle 81' at the same radial distance as the second bended part 112a but at another part of that circle and the inner third bended part 113b is positioned inside both the primary circle 81' and the first bended part 111a. The third inlet rotor interconnection path 113 comprises further a third connecting part 113c connecting the two third bended parts 113a, 113b and two third extension parts 113d, 113e, one (113d) connected to the inner third bended part 113b and reaching out to the primary circle 81' and one (113e) connected to the outer third bended part 113a and reaching in to the primary circle 81'. The fourth inlet rotor interconnection path 114 comprises one inner fourth bended part 114a and one outer fourth bended part 114b. The inner fourth bended part 114a is positioned on a part of the primary circle 81' and the outer fourth bended part 114b is positioned between the first bended part 111a and the inner third bended part 113b. The fourth inlet rotor interconnection path comprises further a fourth connection part 114c connecting the two fourth bended parts 114a, 114b and a fourth extension part connected with the inner fourth bended part 114b and reaching out to the primary circle 81'. The outlet rotor interconnection paths 115, 116, 117, 118 are designed the same but mirrored on the outlet part of the rotary valve (lower part in FIG. 11).

In a first rotor position the first inlet primary valve orifice C1 is connected to the first inlet secondary valve orifice 95a, the second inlet primary valve orifice C2 is connected to the second inlet secondary valve orifice 95b, the third inlet primary valve orifice C3 is connected to a third inlet secondary valve orifice 95c, the fourth inlet primary valve orifice C4 is connected to the fourth inlet secondary valve orifice 95d, the first outlet primary valve orifice C1' is connected to the first outlet secondary valve orifice 95a', the second outlet primary valve orifice C2' is connected to the second outlet secondary valve orifice 95b', the third outlet primary valve orifice C3' is connected to the third outlet secondary valve orifice 95c' and the fourth outlet primary valve orifice C4' is connected to the fourth outlet secondary valve orifice 95d'.

In a second rotor position the first inlet primary valve orifice C1 is connected to the fourth inlet secondary valve orifice 95d, the second inlet primary valve orifice C2 is connected to the first inlet secondary valve orifice 95a, the third inlet primary valve orifice C3 is connected to the second inlet secondary valve orifice 95b, the fourth inlet primary valve orifice C4 is connected to the third inlet secondary valve orifice 95c, the first outlet primary valve orifice C1' is connected to the fourth outlet secondary valve orifice 95d', the second outlet primary valve orifice C2' is connected to the first outlet secondary valve orifice 95a', the third outlet primary valve orifice C3' is connected to the second outlet secondary valve orifice 95b' and the fourth outlet primary valve orifice C4' is connected to the third outlet secondary valve orifice 95c'.

In a third rotor position the first inlet primary valve orifice C1 is connected to the third inlet secondary valve orifice 95c, the second inlet primary valve orifice C2 is connected to the fourth inlet secondary valve orifice 95d, the third inlet primary valve orifice C3 is connected to the first inlet secondary valve orifice 95a, the fourth inlet primary valve orifice C4 is connected to the second inlet secondary valve orifice 95b, the first outlet primary valve orifice C1' is connected to the third outlet secondary valve orifice 95c', the second outlet primary valve orifice C2' is connected to the fourth outlet secondary valve orifice 95d', the third outlet primary valve orifice C3' is connected to the first outlet secondary valve orifice 95a' and the fourth outlet primary valve orifice C4' is connected to the second outlet secondary valve orifice 95b'.

In a fourth rotor position the first inlet primary valve orifice C1 is connected to the second inlet secondary valve orifice 95b, the second inlet primary connection C2 is connected to the third inlet secondary valve orifice 95c, the third inlet primary valve orifice C3 is connected to the fourth inlet secondary valve orifice 95d, the fourth inlet primary valve orifice C4 is connected to the first inlet secondary valve orifice 95a, the first outlet primary valve orifice C1' is connected to the second outlet secondary valve orifice 95b', the second outlet primary valve orifice C2' is connected to the third outlet secondary valve orifice 95c', the third outlet primary valve orifice C3' is connected to the fourth outlet secondary valve orifice 95b' and the fourth outlet primary valve orifice C4' is connected to the first outlet secondary valve orifice 95a'.

Extra column connection ports can be provided in the stator in order to allow column bypass and/or additional set up of columns.

This chromatography system and rotary valve according to the invention can easily be adapted for another number of columns for example three or five columns. Furthermore, the rotor interconnection paths can be at least partly provided as drilled channels inside the rotor. This gives more flexibility to the rotor design and less problems with interfering interconnection paths. For example, some of the rotor interconnection paths can be composed of one partly circular groove in the rotor surface and one or two drilled radial channels below the rotor surface. The partly circular grooves are then provided concentrically around the centre of the rotor and with different radius and the drilled radial channels are provided as reaching out to the position of the primary valve orifices and connected to one of the circular grooves. One secondary valve orifice is positioned within each one of the circular grooves.

The chromatography system and the rotary valve according to the invention can also be adopted for another number of connected columns according to the same principles as disclosed in the embodiments described above. For example, in the embodiment shown in FIG. 8, comprising circular grooves and radial channels additional circular grooves and radial channels are simply added for additional columns in the system. A system using five columns could for example be used if the regeneration step is divided into two steps, one for column cleaning in place and one for equilibration. Even six columns could be used in a system if elution is divided into wash and elution.

Another possibility would be to use a rotary valve according to the description above related to FIGS. 4-9 as either inlet or outlet valve and use other conventional valves for the other sides of the columns, i.e. conventional separate outlet valves for the column outlets if a rotary inlet valve according to the invention is used for the inlet side or conventional separate inlet valves for the columns if a rotary outlet valve according to the invention is used. This should also be covered by this invention.

What is claimed is:

1. A chromatography system comprising at least two chromatography columns, wherein a feed recirculation of outflow from a primary load column to an inlet of a secondary load column is combined in a single, same feed recirculation flow path wherein the feed recirculation outflow from all columns that will be used as primary load columns in the system will pass from outlets of all columns together through the single, same feed recirculation flow path to inlets of all columns.

2. A chromatography system according to claim 1, wherein a feed recirculation detector is provided in the feed recirculation flow path.

3. A chromatography system according to claim 1, comprising a feed recirculation flow uniter connected to outlet valves provided to the outlets from each of the columns that will be used as primary load column, whereby an outlet flow from the columns is controlled such that it is provided to the feed recirculation flow uniter when the column is used as primary load column, said system further comprising a feed recirculation flow splitter connected to the feed recirculation flow uniter through the feed recirculation flow path and further connected to inlet valves provided to inlets to each of the columns that will be used as primary load column, whereby the system is arranged to control the flow from the feed recirculation flow splitter to enter the column that presently serves as secondary load column.

4. A chromatography system according to claim 1, comprising a feed recirculation means connected to outlet valves provided to outlets from each of the columns that will be used as primary load column, whereby the outlet flow from the columns is controlled such that it is provided to the feed recirculation means when the column is used as primary load column, said feed recirculation means further being connected to inlet valves provided to inlets to each of the columns that will be used as primary load column, whereby the system is arranged to control the flow from the feed recirculation means to enter the column that presently serves as secondary load column, said feed recirculation means further comprising a feed recirculation flow path through which all feed recirculation flow will pass.

5. A chromatography system according to claim 1, wherein said system comprises
a column inlet rotary valve connected to the inlets of all columns that will be used as primary load columns in the system and to at least three inflows, and
a column outlet rotary valve connected to the outlets of all columns that will be used as primary load columns in the system and to at least three outflows, wherein the feed recirculation flow path connects the inlet rotary valve with the outlet rotary valve.

6. A chromatography system according to claim 1, wherein said system comprises
a column connection rotary valve connected to the inlets of all columns that will be used as primary load columns in the system and to at least three inflows and connected to the outlets of all columns that will be used as primary load columns in the system and to at least three outflows, wherein said feed recirculation flow path connects each column outlet to each column inlet through the column connection rotary valve.

7. A method for recirculating outlet flow from a primary load column to the inlet of a secondary load column in a chromatography system comprising at least two chromatography columns, said method comprising:
combining in a single, same feed recirculation flow path, the feed recirculation for all columns that will be used as primary load columns in the system such that the feed recirculation flow will pass from outlets of all columns together through the single, same feed recirculation flow path to inlets of all columns.

8. A method according to claim 7, further comprising detecting an effluent signal being representative of the composition of the feed recirculation in the feed recirculation flow path.

9. A method according to claim 7, further comprising directing outflow from each of the columns when they are serving as primary load column to a feed recirculation flow uniter connected to outlet valves provided to outlets from each of the columns that will be used as primary load column, transferring said outflow from the feed recirculation flow uniter through the feed recirculation flow path to a feed recirculation flow splitter connected to inlet valves provided to inlets to each of the columns that will be used as primary load column, and controlling the flow from the feed recirculation flow splitter to enter the column that presently serves as secondary load column.

* * * * *